(12) United States Patent
Liu et al.

(10) Patent No.: US 9,895,346 B2
(45) Date of Patent: Feb. 20, 2018

(54) APPLICATIONS OF SUBSTITUENT BENZYLOXY GROUP CONTAINING ETHER COMPOUNDS FOR PREPARING ANTITUMOR DRUGS

(71) Applicants: Sinochem Corporation, Beijing (CN); Shenyang Research Institute Of Chemical Industry Co., Ltd., Shenyang, Liaoning (CN)

(72) Inventors: Changling Liu, Liaoning (CN); Aiying Guan, Liaoning (CN); Xiaoping Yang, Liaoning (CN); Baoshan Chai, Liaoning (CN)

(73) Assignees: Sinochem Corporation, Beijing (CN); Shenyang Research Institute of Chemical Industry Co., Ltd., Shenyang (CN)

( * ) Notice: Subject to any disclaimer, the term of this patent is extended or adjusted under 35 U.S.C. 154(b) by 186 days.

(21) Appl. No.: 14/909,124

(22) PCT Filed: Aug. 22, 2014

(86) PCT No.: PCT/CN2014/084990
§ 371 (c)(1),
(2) Date: Jan. 31, 2016

(87) PCT Pub. No.: WO2015/027863
PCT Pub. Date: Mar. 5, 2015

(65) Prior Publication Data
US 2017/0296508 A1 Oct. 19, 2017

(30) Foreign Application Priority Data

Aug. 27, 2013 (CN) .......................... 2013 1 0377438
Aug. 27, 2013 (CN) .......................... 2013 1 0377457

(51) Int. Cl.
*A61K 31/366* (2006.01)
*A61K 31/415* (2006.01)
*A61K 31/505* (2006.01)
*A61K 31/216* (2006.01)

(52) U.S. Cl.
CPC .......... *A61K 31/366* (2013.01); *A61K 31/216* (2013.01); *A61K 31/415* (2013.01); *A61K 31/505* (2013.01)

(58) Field of Classification Search
None
See application file for complete search history.

(56) References Cited

U.S. PATENT DOCUMENTS

| | | | | |
|---|---|---|---|---|
| 2012/0088662 A1* | 4/2012 | Dietz | .................... | A01N 37/34 504/100 |
| 2012/0149707 A1* | 6/2012 | Kim | ..................... | C07C 69/736 514/238.5 |

FOREIGN PATENT DOCUMENTS

CN 102600164 A 7/2012

OTHER PUBLICATIONS

International Search Report received in PCT/CN2014/084990, dated Nov. 28, 2014.
International Written Opinion received in PCT/CN2014/084990, dated Nov. 28, 2014.

* cited by examiner

*Primary Examiner* — Bong-Sook Baek
(74) *Attorney, Agent, or Firm* — Suzannah K. Sundby, Esq.; Canady + Lortz LLP

(57) ABSTRACT

Disclosed are applications of substituent benzyloxy group containing ether compounds represented by general formula I for preparing antitumor drugs.

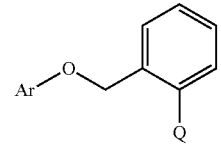

I

The definition of the substituent groups in the formula I are provided in the specification.
The compounds having general formula I have desirable antitumor activity, particularly, and have excellent activity against leukemia strain HL-60, lung cancer A549, H157, H460, H520, bladder cancer T24, J82, prostate cancer LNCap, PC-3, rectal cancer HCT8, HCT116, RkO and the like.

13 Claims, No Drawings

APPLICATIONS OF SUBSTITUENT BENZYLOXY GROUP CONTAINING ETHER COMPOUNDS FOR PREPARING ANTITUMOR DRUGS

FIELD OF THE INVENTION

The present invention belongs to the field of medicine, relating to the field of antitumor drugs. Specifically to applications of substituent benzyloxy group containing ether compounds for preparing antitumor drugs.

BACKGROUND OF THE INVENTION

The following journals and patents disclosed benzopyrone compounds containing methoxyacrylate with fungicidal activity in agrochemical field: Pest Management Science, Volume: 67, Issue: 6, Pages: 647-655; Natural Product Communications, Volume: 6, Issue: 12, Pages: 1917-1920; Nongyao, Volume: 50, Issue: 2, Pages: 90-92; Nongyaoxue Xuebao, Volume: 12, Issue: 4, Pages: 453-457; Natural Product Communications, Volume: 2, Issue: 8, Pages: 845-848; Chinese Chemical Letters, Volume: 22, Issue: 6, Pages: 663-666; WO 2005044813.

Journal of Medicinal Chemistry, Volume: 50, Issue: 12, Pages: 2886-2895 reported the following general formula containing benzopyrone group with antiplatelet activity.

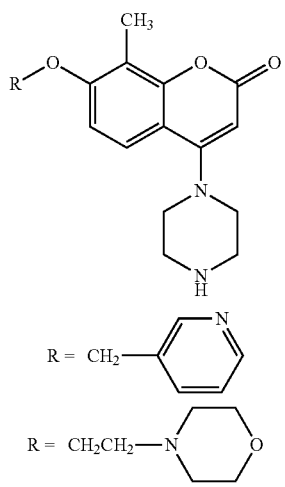

Bioorganic & Medicinal Chemistry Letters 23(2013) 3505-3510 disclosed a strobilurin compound containing substituted pyrimidinamines with some antitumor activity, the structure of compound 96 (compound A in this patent) is as follows:

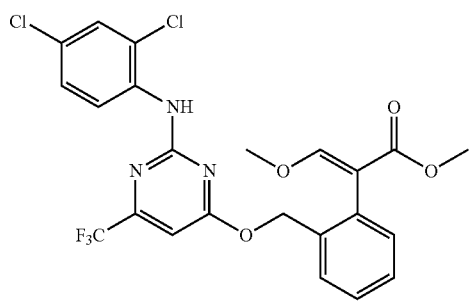

Patent U.S. Pat. No. 6,084,120 disclosed the compound having following general formula has some inhibition effect on *Plasmodium falciparum* NF54 strain and *plasmodium berghei*, however, compound B was reported at the same time without any biological data. Patent U.S. Pat. No. 7,947,734 also disclosed compound B (that is flufenoxystrobin) with good fungicidal and acaricidal activity in agrochmical field.

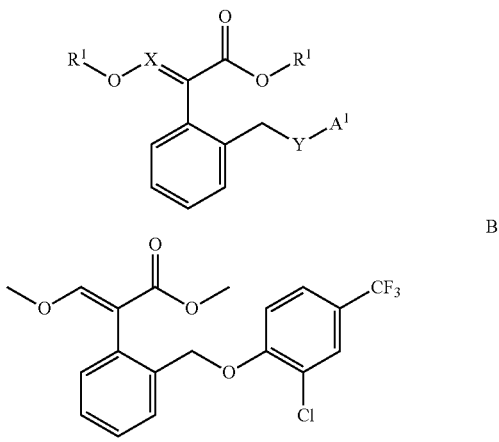

In the prior art, the substituent benzyloxy group containing ether compounds having the structure of general formula I were not reported as antitumor agents.

SUMMARY OF THE INVENTION

The object of the present invention is to provide substituent benzyloxy group containing ether compounds having general formula I, which can be applied to prepare antitumor drugs.

Detailed Description of the Invention is as Follows:

The application of substituent benzyloxy group containing ether compounds for preparing antitumor drugs, the compounds having the structure of general formula I:

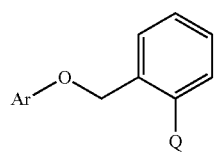

Wherein:

Ar is selected from one of the following groups, Ar1 to Ar16:

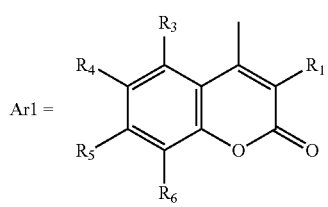

-continued
Ar2 = 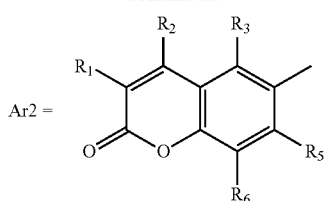
Ar3 = 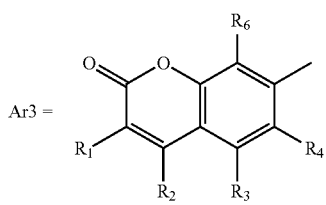
Ar4 = 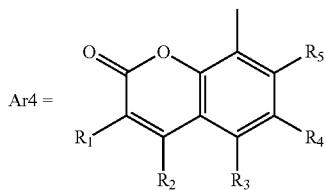
Ar5 = 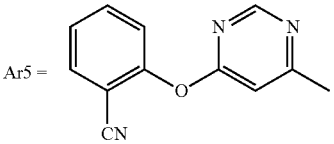
Ar6 = 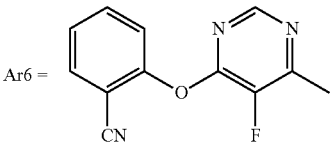
Ar7 = 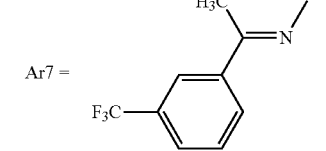
Ar8 = 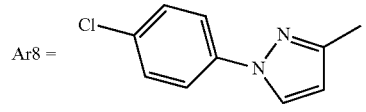
Ar9 = 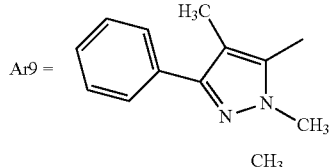
Ar10 = 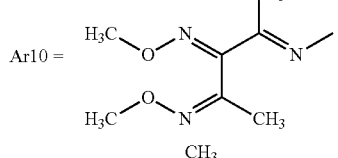
Ar11 = 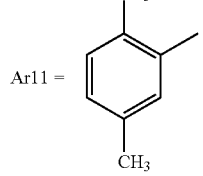
-continued
Ar12 = 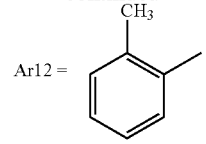
Ar13 = 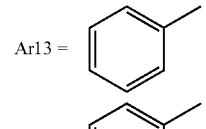
Ar14 = 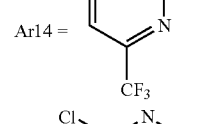
Ar15 = 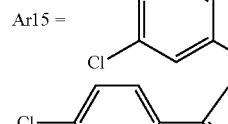
Ar16 = 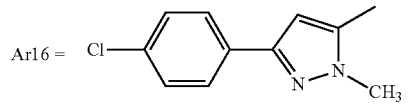
Q is selected from one of the following groups, Q1 to Q22:
Q1 = 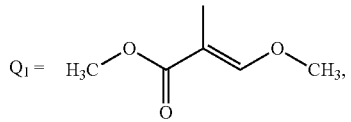
Q2 = 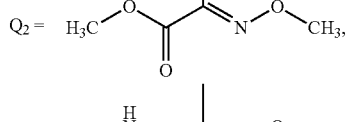
Q3 = 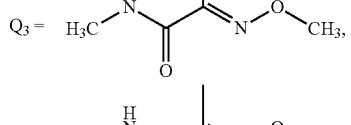
Q4 = 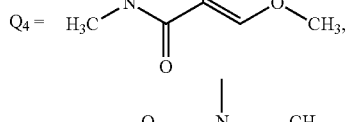
Q5 = 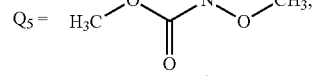
Q6 = 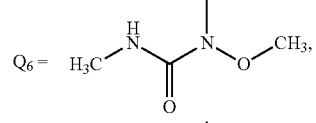
Q7 = 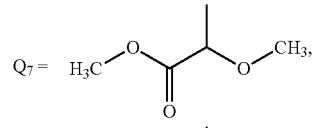
Q8 = 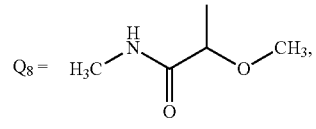

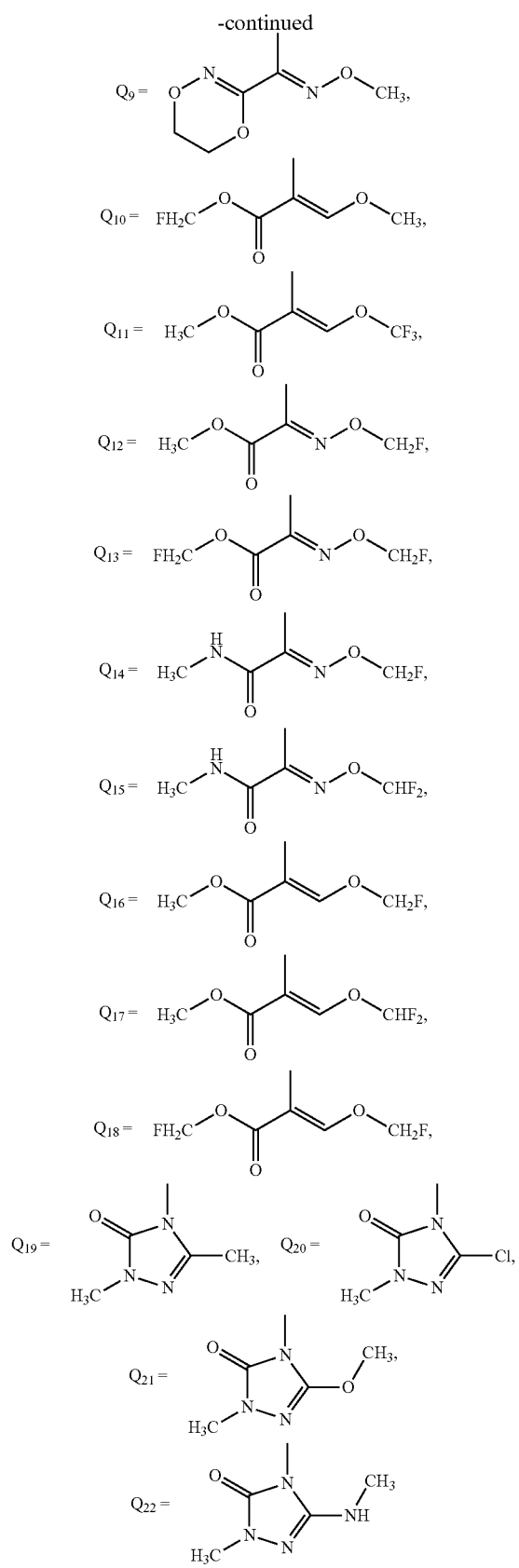

$R_1$, $R_2$, $R_3$, $R_4$, $R_5$, $R_6$ mutually independently may be the same or different, selected from H, halo, CN, $NO_2$, OH, $NH_2$, CHO, $CO_2H$, $CO_2Na$, $CO_2NH_4$, $C_1$-$C_{12}$alkyl, $C_1$-$C_{12}$haloalkyl, $C_3$-$C_8$cycloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkoxy$C_1$-$C_{12}$alkyl 、halo$C_1$-$C_{12}$alkoxy$C_1$-$C_{12}$alkyl 、$C_1$-$C_{12}$alkoxy$C_1$-$C_{12}$alkoxy 、halo$C_1$-$C_{12}$alkoxy$C_1$-$C_{12}$alkoxy 、$C_1$-$C_{12}$alkylthio$C_1$-$C_{12}$alkyl 、halo$C_1$-$C_{12}$alkylthio$C_1$-$C_{12}$alkyl 、$C_1$-$C_{12}$alkylamino 、$C_1$-$C_{12}$haloalkylamino 、$C_2$-$C_{12}$dialkylamino 、$C_2$-$C_{12}$halodialkylamino 、piperidinyl、pyrrolidinyl、N-methylpiperidinyl、morpholinyl、$C_2$-$C_{12}$alkenyl 、$C_2$-$C_{12}$haloalkenyl、$C_2$-$C_{12}$alkynyl 、$C_2$-$C_{12}$haloalkynyl、$C_2$-$C_{12}$alkenyloxy、$C_2$-$C_{12}$haloalkenyloxy、$C_2$-$C_{12}$alkynyloxy、$C_2$-$C_{12}$haloalkynyloxy 、$C_1$-$C_{12}$alkylsulfonyl 、$C_1$-$C_{12}$haloalkylsulfonyl 、$C_1$-$C_{12}$alkylsulfinyl 、$C_1$-$C_{12}$haloalkylsulfinyl 、$C_1$-$C_{12}$alkylcarbonyl 、$C_1$-$C_{12}$haloalkylcarbonyl 、$C_1$-$C_{12}$alkylcarbonyloxy 、$C_1$-$C_{12}$alkylcarbonylamino 、$C_1$-$C_{12}$alkylsulfonyloxy 、$C_1$-$C_{12}$alkoxycarbonyl 、$C_1$-$C_{12}$haloalkoxycarbonyl 、$C_1$-$C_{12}$alkylaminosulfonyl 、$C_1$-$C_{12}$alkoxycarbonylamino 、$C_1$-$C_{12}$alkoxycarbonyl$C_1$-$C_{12}$alkyl 、$C_1$-$C_{12}$alkoxycarbonyl$C_1$-$C_{12}$alkoxy 、amino$C_1$-$C_{12}$alkyl 、$C_1$-$C_{12}$alkylamino$C_1$-$C_{12}$alkyl 、$C_2$-$C_{12}$dialkylamino$C_1$-$C_{12}$alkyl、$C(=O)NR_{10}R_{11}$ 、$OC(=O)NR_{10}R_{11}$ 、$C(=S)NR_{10}R_{11}$ 、$SO_2NR_{10}R_{11}$ 、$C(=NOR_9)R_8$ or $R_7$; or $R_1$, $R_2$ and carbon atom linked to them form five, six or seven-membered ring;

$R_7$ is selected from unsubstituted or substituted phenyl, phenyloxy, phenyloxy $C_1$-$C_{12}$alkyl 、phenylcarbonyl 、phenyloxycarbonyl、phenylaminocarbonyl、phenyl$C_1$-$C_{12}$alkyl、phenyl$C_1$-$C_{12}$alkoxy 、phenyl$C_1$-$C_{12}$alkoxy$C_1$-$C_{12}$alkyl 、naphthyl、naphthyloxy 、naphthyloxy $C_1$-$C_{12}$alkyl 、naphthylcarbonyl 、naphthyl $C_1$-$C_{12}$alkyl 、naphthyl $C_1$-$C_{12}$alkoxy 、naphthyl $C_1$-$C_{12}$alkoxy$C_1$-$C_{12}$alkyl、heteroaryl、heteroaryloxy、heteroaryl$C_1$-$C_{12}$alkoxy$C_1$-$C_{12}$alkyl、heteroaryloxy$C_1$-$C_{12}$alkyl、heteroarylcarbonyl、heteroaryloxycarbonyl、heteroarylaminocarbonyl、heteroaryl$C_1$-$C_{12}$alkyl or heteroaryl$C_1$-$C_{12}$alkoxy, which is further mutually independently optionally substituted by 1 to 5 following group(s): halo 、$NO_2$、CN 、SH 、$C_1$-$C_6$alkyl 、$C_1$-$C_6$ halo alkyl 、$C_3$-$C_8$ cycloalkyl 、$C_1$-$C_6$alkoxy 、$C_1$-$C_6$ halo alkoxy 、$C_1$-$C_6$alkylthio 、$C_1$-$C_6$ halo alkylthio 、$C_2$-$C_6$alkenyl 、$C_2$-$C_6$ halo alkenyl 、$C_2$-$C_6$alkynyl 、halo alkynyl 、$C_3$-$C_6$alkenyloxy 、$C_3$-$C_6$ halo alkenyloxy 、$C_3$-$C_6$alkynyloxy 、$C_3$-$C_6$ halo alkynyloxy 、$C_1$-$C_6$alkylsulfinyl 、$C_1$-$C_6$ halo alkylsulfinyl 、$C_1$-$C_6$alkylsulfonyl 、$C_1$-$C_6$ halo alkylsulfonyl 、$C_1$-$C_6$alkoxy$C_1$-$C_6$alkyl 、$C_1$-$C_6$alkylcarbonyl 、$C_1$-$C_6$ halo alkylcarbonyl 、$C_1$-$C_6$alkylcarbonyloxy 、$C_1$-$C_6$alkylcarbonylamino 、$C_1$-$C_6$alkylsulfonyloxy 、$C_1$-$C_6$alkoxycarbonyl 、$C_1$-$C_6$alkoxy$C_1$-$C_6$alkoxy 、$C_1$-$C_6$alkoxycarbonyl$C_1$-$C_6$alkyl 、$C_1$-$C_6$alkoxycarbonylamino 、$C_1$-$C_6$alkoxycarbonyl$C_1$-$C_6$alkoxy 、CHO 、$CO_2H$ 、$CO_2Na$ 、$CO_2NH_4$ 、$NR_{10}R_{11}$ 、$C(=O)NR_{10}R_{11}$ 、$OC(=O)NR_{10}R_{11}$ 、$C(=S)NR_{10}R_{11}$ or $SO_2NR_{10}R_{11}$:

$R_8$, $R_9$ is mutually independently selected from H、$C_1$-$C_6$alkyl、aryl or aryl $C_1$-$C_6$ alkyl;

$R_{10}$, $R_{11}$ mutually independently may be the same or different、selected from H 、$C_1$-$C_6$alkyl 、$C_1$-$C_6$ halo alkyl 、$C_1$-$C_6$alkoxy 、$C_1$-$C_6$ halo alkoxy 、$C_1$-$C_6$alkylthio 、$C_1$-$C_6$ halo alkylthio or $C_3$-$C_8$cycloalkyl;

And their stereoisomers.

The preferred substituent benzyloxy group containing ether compounds above compounds applied as antitumor drugs of general formula I of this invention are:

Ar is selected from Ar1、Ar2、Ar3、Ar4 or Ar16;

Q is selected from $Q_1$、$Q_2$、$Q_3$、$Q_4$、$Q_5$、$Q_6$、$Q_7$、$Q_8$、$Q_9$、$Q_{19}$、$Q_{20}$、$Q_{21}$ or $Q_{22}$:

$R_1, R_2, R_3, R_4, R_5, R_6$ mutually independently may be the same or different, selected from H, halo, CN, $NO_2$, OH, $NH_2$, CHO, $CO_2H$, $CO_2Na$, $CO_2NH_4$, $C_1$-$C_6$alkyl, $C_1$-$C_6$haloalkyl, $C_3$-$C_6$cycloalkyl, $C_1$-$C_6$alkoxy, $C_1$-$C_6$haloalkoxy, $C_1$-$C_6$alkylthio, $C_1$-$C_6$haloalkylthio, $C_1$-$C_6$alkoxy$C_1$-$C_6$alkyl、halo$C_1$-$C_6$alkoxy$C_1$-$C_6$alkyl、$C_1$-$C_6$alkoxy$C_1$-$C_6$alkoxy、halo$C_1$-$C_6$alkoxy$C_1$-$C_6$alkoxy、$C_1$-$C_6$alkylthio$C_1$-$C_6$alkyl、halo$C_1$-$C_6$alkylthio$C_1$-$C_6$alkyl、$C_1$-$C_6$alkylamino、$C_1$-$C_6$haloalkylamino、$C_2$-$C_8$dialkylamino、$C_2$-$C_8$halodialkylamino、piperidinyl、pyrrolidinyl、N-methylpiperidinyl、morpholinyl、$C_2$-$C_6$alkenyl、$C_2$-$C_6$haloalkenyl、$C_2$-$C_6$alkynyl、$C_2$-$C_6$haloalkynyl、$C_2$-$C_6$alkenyloxy、$C_2$-$C_6$haloalkenyloxy、$C_2$-$C_6$alkynyloxy、$C_2$-$C_6$haloalkynyloxy、$C_1$-$C_6$alkylsulfonyl、$C_1$-$C_6$haloalkylsulfonyl、$C_1$-$C_6$alkylsulfinyl、$C_1$-$C_6$haloalkylsulfinyl、$C_1$-$C_6$alkylcarbonyl、$C_1$-$C_6$haloalkylcarbonyl、$C_1$-$C_6$alkylcarbonyloxyl、$C_1$-$C_6$alkylcarbonylamino、$C_1$-$C_6$alkylsulfonyloxy、$C_1$-$C_6$alkoxycarbonyl、$C_1$-$C_6$haloalkoxycarbonyl、$C_1$-$C_6$alkylaminosulfonyl、$C_1$-$C_6$alkoxycarbonylamino、$C_1$-$C_6$alkoxycarbonyl$C_1$-$C_6$alkyl、$C_1$-$C_6$alkoxycarbonyl$C_1$-$C_6$alkoxy、amino$C_1$-$C_6$alkyl、$C_1$-$C_6$alkylamino$C_1$-$C_6$alkyl、$C_2$-$C_8$dialkylamino$C_1$-$C_6$alkyl、$C(=O)NR_{10}R_{11}$、$OC(=O)NR_{10}R_{11}$、$C(=S)NR_{10}R_{11}$、$SO_2NR_{10}R_{11}$, $C(=NOR_9)R_8$ or $R_7$; or $R_1$, $R_2$ and carbon atom linked to them form five or six-membered ring;

$R_7$ is selected from unsubstituted or substituted phenyl, phenyloxy, phenyloxy $C_1$-$C_6$alkyl、phenylcarbonyl、phenyloxycarbonyl、phenylaminocarbonyl、phenyl$C_1$-$C_6$alkyl、phenyl$C_1$-$C_6$alkoxy、phenyl$C_1$-$C_6$alkoxy$C_1$-$C_6$alkyl、naphthyl、naphthyloxy、naphthyloxy $C_1$-$C_6$alkyl、naphthylcarbonyl、naphthyl $C_1$-$C_6$alkyl、naphthyl $C_1$-$C_6$alkoxy、naphthyl$C_1$-$C_6$alkoxy$C_1$-$C_6$alkyl、heteroaryl、heteroaryloxy、heteroaryl$C_1$-$C_6$alkoxy$C_1$-$C_6$alkyl、heteroaryloxy$C_1$-$C_6$alkyl、heteroarylcarbonyl、heteroaryloxycarbonyl、heteroarylaminocarbonyl、heteroaryl$C_1$-$C_6$alkyl or heteroaryl$C_1$-$C_6$alkoxy, which is further mutually independently optionally substituted by 1 to 5 following group(s): halo、$NO_2$、SH、$C_1$-$C_4$alkyl、$C_1$-$C_4$ haloalkyl、$C_3$-$C_6$cycloalkyl、$C_1$-$C_4$alkoxy、$C_1$-$C_4$ halo alkoxy、$C_1$-$C_4$alkylthio、$C_1$-$C_4$ halo alkylthio、$C_2$-$C_4$alkenyl、$C_2$-$C_4$ halo alkenyl、$C_2$-$C_4$alkynyl、$C_2$-$C_4$ halo alkynyl、$C_3$-$C_4$alkenyloxy、$C_3$-$C_4$halo alkenyloxy、$C_3$-$C_4$alkynyloxy、$C_3$-$C_4$ halo alkynyloxy、$C_1$-$C_4$alkylsulfinyl、$C_1$-$C_4$ halo alkylsulfinyl、$C_1$-$C_4$alkylsulfonyl、$C_1$-$C_4$ halo alkylsulfonyl、$C_1$-$C_4$alkoxy$C_1$-$C_4$alkyl、$C_1$-$C_4$alkylcarbonyl、$C_1$-$C_4$ halo alkylcarbonyl、$C_1$-$C_4$alkylcarbonyloxy、$C_1$-$C_4$alkylcarbonylamino、$C_1$-$C_4$alkylsulfonyloxy、$C_1$-$C_4$alkoxycarbonyl、$C_1$-$C_4$alkoxy$C_1$-$C_4$alkoxy、$C_1$-$C_4$alkoxycarbonyl$C_1$-$C_4$alkyl、$C_1$-$C_4$alkoxycarbonylamino、$C_1$-$C_4$alkoxycarbonyl$C_1$-$C_4$alkoxy、CHO、$CO_2H$、$CO_2Na$、$CO_2NH_4$、$NR_{10}R_{11}$、$C(=O)NR_{10}R_{11}$、$OC(=O)NR_{10}R_{11}$、$C(=S)NR_{10}R_{11}$ or $SO_2NR_{10}R_{11}$:

$R_8$, $R_9$ is mutually independently selected from H、$C_1$-$C_4$alkyl、aryl or aryl $C_1$-$C_4$alkyl;

$R_{10}$, $R_{11}$ mutually independently may be the same or different、selected from $C_1$-$C_4$alkyl、$C_1$-$C_4$ halo alkyl、$C_1$-$C_4$alkoxy、$C_1$-$C_4$ halo alkoxy、$C_1$-$C_4$alkylthio、$C_1$-$C_4$ halo alkylthio or $C_3$-$C_6$cycloalkyl.

The preferred substituent benzyloxy group containing ether compounds above compounds applied as antitumor drugs of general formula I of this invention are:

Ar is selected from Ar1, Ar2, Ar3, Ar4 or Ar16;

Q is selected from $Q_1$、$Q_2$、$Q_3$、$Q_4$、$Q_5$、$Q_6$、$Q_7$、$Q_8$、$Q_9$、$Q_{19}$、$Q_{20}$、$Q_{21}$、or $Q_{22}$:

$R_1, R_2, R_3, R_4, R_5, R_6$ mutually independently may be the same or different, selected from H, halo, CN, $NO_2$, OH, $NH_2$, CHO, $CO_2H$, $CO_2Na$, $CO_2NH_4$, $C_1$-$C_6$alkyl, $C_1$-$C_6$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkoxy$C_1$-$C_4$alkyl、halo$C_1$-$C_4$alkoxy$C_1$-$C_4$alkyl、$C_1$-$C_4$alkoxy$C_1$-$C_4$alkoxy、halo$C_1$-$C_4$alkoxy$C_1$-$C_4$alkoxy、$C_1$-$C_4$alkylthio$C_1$-$C_4$alkyl、halo$C_1$-$C_4$alkylthio$C_1$-$C_4$alkyl、$C_1$-$C_4$alkylamino、$C_1$-$C_4$haloalkylamino、$C_2$-$C_6$dialkylamino、$C_2$-$C_6$halodialkylamino、piperidinyl、pyrrolidinyl、N-methylpiperidinyl、morpholinyl、$C_2$-$C_4$alkenyl、$C_2$-$C_4$haloalkenyl、$C_2$-$C_4$alkynyl、$C_2$-$C_4$haloalkynyl、$C_2$-$C_4$alkenyloxy、$C_2$-$C_4$haloalkenyloxy、$C_2$-$C_4$alkynyloxy、$C_1$-$C_4$alkylsulfonyl、$C_1$-$C_4$haloalkylsulfonyl、$C_1$-$C_4$alkylsulfinyl、$C_1$-$C_4$haloalkylsulfinyl、$C_1$-$C_4$alkylcarbonyl、$C_1$-$C_4$haloalkylcarbonyl、$C_1$-$C_4$alkylcarbonyloxy、$C_1$-$C_4$alkylcarbonylamino、$C_1$-$C_4$alkylsulfonyloxy、$C_1$-$C_4$alkoxycarbonyl、$C_1$-$C_4$haloalkoxycarbonyl、$C_1$-$C_4$alkylaminosulfonyl、$C_1$-$C_4$alkoxycarbonylamino、$C_1$-$C_4$alkoxycarbonyl$C_1$-$C_4$alkyl、$C_1$-$C_4$alkoxycarbonyl$C_1$-$C_4$alkoxy、amino$C_1$-$C_4$alkyl、$C_1$-$C_4$alkylamino$C_1$-$C_4$alkyl、$C_2$-$C_6$dialkylamino$C_1$-$C_4$alkyl、$C(=O)NR_{10}R_{11}$、$OC(=O)NR_{10}R_{11}$、$C(=S)NR_{10}R_{11}$、$SO_2NR_{10}R_{11}$、$C(=NOR_9)R_8$ or $R_7$; or $R_1$, $R_2$ and carbon atom linked to them form saturated five or six-membered ring;

$R_7$ is selected from unsubstituted or substituted phenyl、phenyloxy、phenyloxy $C_1$-$C_4$alkyl、phenylcarbonyl、phenyloxycarbonyl、phenylaminocarbonyl、phenyl$C_1$-$C_4$alkyl、phenyl$C_1$-$C_4$alkoxy、phenyl$C_1$-$C_4$alkoxy$C_1$-$C_4$alkyl、naphthyl、naphthyloxy、naphthyloxy $C_1$-$C_4$alkyl、naphthylcarbonyl、naphthyl $C_1$-$C_4$alkoxy、naphthyl$C_1$-$C_4$alkoxy$C_1$-$C_4$alkyl、heteroaryl、heteroaryloxy、heteroaryl$C_1$-$C_4$alkoxy$C_1$-$C_4$alkyl、heteroaryloxy$C_1$-$C_4$alkyl、heteroarylcarbonyl、heteroaryloxycarbonyl、heteroarylaminocarbonyl、heteroaryl$C_1$-$C_4$alkyl or heteroaryl$C_1$-$C_4$alkoxy、which is further mutually independently optionally substituted by 1 to 5 following group(s): halo、$NO_2$、CN、SH、$C_1$-$C_4$alkyl、$C_1$-$C_4$ haloalkyl、$C_3$-$C_6$cycloalkyl、$C_1$-$C_4$alkoxy、$C_1$-$C_4$haloalkoxy、$C_1$-$C_4$alkylthio、$C_1$-$C_4$ halo alkylthio、$C_2$-$C_4$alkenyl、$C_2$-$C_4$ halo alkenyl、$C_2$-$C_4$alkynyl、$C_2$-$C_4$ halo alkynyl、$C_3$-$C_4$alkenyloxy、$C_3$-$C_4$halo alkenyloxy、$C_3$-$C_4$alkynyloxy、$C_3$-$C_4$ haloalkynyloxy、$C_1$-$C_4$alkylsulfinyl、$C_1$-$C_4$ halo alkylsulfinyl、$C_1$-$C_4$alkylsulfonyl、$C_1$-$C_4$ halo alkylsulfonyl、$C_1$-$C_4$alkoxy$C_1$-$C_4$alkyl、$C_1$-$C_4$alkylcarbonyl、$C_1$-$C_4$ halo alkylcarbonyl、$C_1$-$C_4$alkylcarbonyloxy、$C_1$-$C_4$alkylcarbonylamino、$C_1$-$C_4$alkylsulfonyloxy、$C_1$-$C_4$alkoxycarbonyl、$C_1$-$C_4$alkoxy$C_1$-$C_4$alkoxy、$C_1$-$C_4$alkoxycarbonyl$C_1$-$C_4$alkyl、$C_1$-$C_4$alkoxycarbonylamino、$C_1$-$C_4$alkoxycarbonyl$C_1$-$C_4$alkoxy、CHO、$CO_2H$、$CO_2Na$、$CO_2NH_4$、$NR_{10}R_{11}$、$C(=O)NR_{10}R_{11}$、$OC(=O)NR_{10}R_{11}$、$C(=S)NR_{10}R_{11}$ or $SO_2NR_{10}R_{11}$:

$R_8$, $R_9$ is mutually independently selected from H、$C_1$-$C_4$alkyl、aryl or aryl $C_1$-$C_4$alkyl;

$R_{10}$, $R_{11}$ mutually independently may be the same or different 、 selected from H 、 $C_1$-$C_4$alkyl 、 $C_1$-$C_4$ haloalkyl 、 $C_1$-$C_4$alkoxyl 、 $C_1$-$C_4$ haloalkoxy 、 $C_1$-$C_4$alkylthio 、 $C_1$-$C_4$ haloalkylthio or $C_3$-$C_6$cycloalkyl.

Furthermore, the preferred substituent benzyloxy group containing ether compounds above compounds applied as antitumor drugs of general formula I of this invention are:

Ar is selected from Ar1 、 Ar2 、 Ar3 or Ar16;

Q is selected from $Q_1$ 、 $Q_2$ 、 $Q_3$ 、 $Q_4$ 、 $Q_5$ 、 $Q_6$ 、 $Q_7$ or $Q_8$;

$R_1$, $R_2$, $R_3$, $R_4$, $R_5$, $R_6$ mutually independently may be the same or different, selected from H, halo, CN, $C_1$-$C_6$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$alkoxy$C_1$-$C_4$alkyl 、 $C_1$-$C_4$alkylamino 、 $C_2$-$C_6$dialkylamino 、 $C_1$-$C_4$alkylsulfonyl or $R_7$; or $R_1$, $R_2$ and carbon atom linked to them form saturated five or six-membered ring;

$R_7$ is selected from unsubstituted or substituted phenyl, benzyl, phenylethyl or heteroaryl, which is further mutually independently optionally substituted by 1 to 5 following group(s): halo 、 $NO_2$ 、 CN 、 $C_1$-$C_4$ alkyl 、 $C_1$-$C_4$ haloalkyl 、 $C_1$-$C_4$alkoxy or $C_1$-$C_4$ haloalkoxy.

Furthermore, the preferred substituent benzyloxy group containing ether compounds above compounds applied as antitumor drugs of general formula I of this invention are:

Ar is selected from Ar1, Ar2, Ar3 or Ar16;

Q is $Q_1$;

$R_1$, $R_2$, $R_3$, $R_4$, $R_5$, $R_6$ mutually independently may be the same or different, selected from H, halo, CN, $C_1$-$C_6$alkyl, $C_1$-$C_4$haloalkyl or $R_7$; or $R_1$, $R_2$ and carbon atom linked to them form saturated five or six-membered ring;

$R_7$ is selected from unsubstituted or substituted phenyl, benzyl or heteroaryl, which is further mutually independently optionally substituted by 1 to 5 following group(s): halo 、 $NO_2$ 、 CN 、 $C_1$-$C_4$alkyl 、 $C_1$-$C_4$ haloalkyl 、 $C_1$-$C_4$alkoxy or $C_1$-$C_4$ haloalkoxy.

Furthermore, the preferred substituent benzyloxy group containing ether compounds above compounds applied as antitumor drugs of general formula I of this invention are:

Ar is selected from Ar3 or Ar16;

Q is $Q_1$;

$R_1$, $R_2$, $R_3$, $R_4$, $R_5$, $R_6$ mutually independently may be the same or different, selected from H, halo, CN, $C_1$-$C_6$alkyl, $C_1$-$C_4$haloalkyl or $R_7$; or $R_1$, $R_2$ and carbon atom linked to them form saturated five or six-membered ring;

$R_7$ is selected from unsubstituted or substituted phenyl, benzyl or heteroaryl, which is further mutually independently optionally substituted by 1 to 5 following group(s): halo 、 $NO_2$ 、 CN 、 $C_1$-$C_4$alkyl 、 $C_1$-$C_4$ haloalkyl 、 $C_1$-$C_4$alkoxy or $C_1$-$C_4$ haloalkoxy.

Furthermore, the preferred substituent benzyloxy group containing ether compounds above compounds applied as antitumor drugs of general formula I of this invention are:

Ar is selected from Ar3 or Ar16;

Q is $Q_1$;

$R_1$ is selected from H, halo or $C_1$-$C_6$alkyl;

$R_2$ is selected from $C_1$-$C_4$alkyl, $C_1$-$C_4$haloalkyl or $R_7$;

Or $R_1$, $R_2$ and carbon atom linked to them form saturated five or six-membered ring;

$R_3$, $R_4$ are H;

$R_6$ is selected from H or $C_1$-$C_4$alkyl;

$R_7$ is selected from unsubstituted or substituted phenyl, which is further mutually independently optionally substituted by 1 to 3 following group(s): halo, CN, $C_1$-$C_4$alkyl, $C_1$-$C_4$ haloalkyl, $C_1$-$C_4$alkoxy or $C_1$-$C_4$ haloalkoxy.

Furthermore, the preferred substituent benzyloxy group containing ether compounds above compounds applied as antitumor drugs of general formula I of this invention are:

Ar is selected from Ar3 or Ar16;

Q is $Q_1$;

$R_1$ is selected from H, halo or $C_1$-$C_6$alkyl;

$R_2$ is selected from $C_1$-$C_4$alkyl or $R_7$;

Or $R_1$, $R_2$ and carbon atom linked to them form saturated five or six-membered ring;

$R_3$, $R_4$ are H;

$R_6$ is selected from H or $C_1$-$C_4$alkyl;

$R_7$ is selected from unsubstituted or substituted phenyl, which is further mutually independently optionally substituted by 1 to 3 following group(s): halo, $C_1$-$C_4$alkyl, $C_1$-$C_4$alkoxy or $C_1$-$C_4$ haloalkoxy.

The more preferred substituent benzyloxy group containing ether compounds above compounds applied as antitumor drugs of general formula I of this invention are:

Ar is selected from Ar3 or Ar16;

Q is $Q_1$;

$R_1$ is selected from H, F or $C_1$-$C_4$alkyl;

$R_2$ is selected from $C_1$-$C_4$alkyl or phenyl;

Or $R_1$, $R_2$ and carbon atom linked to them form saturated six-membered ring;

$R_3$, $R_4$ are H;

$R_6$ is selected from H or $CH_3$.

The most preferred substituent benzyloxy group containing ether compounds applied as antitumor drugs of general formula I of this invention are:

Ar is selected from Ar3 or Ar16;

Q is $Q_1$;

$R_1$ is selected from H or $C_1$-$C_4$alkyl;

$R_2$ is selected from $CH_3$ or phenyl;

Or $R_1$, $R_2$ and carbon atom linked to them form saturated six-membered ring;

$R_3$, $R_4$, $R_6$ are H.

The terms used above to definite the compounds of general formula I represent substitutes as follow:

The "halogen" or "halo" is fluorine, chlorine, bromine or iodine.

The "alkyl" stands for straight or branched chain alkyl, such as methyl, ethyl, propyl, isopropyl or tert-butyl. The "haloalkyl" stands for straight or branched chain alkyl, in which hydrogen atoms can be all or partly substituted with halogen, such as chloromethyl, dichloromethyl, trichlororaethyl, fluoromethyl, difluoromethyl, trifluoromethyl, etc.

The "alkoxy" refers to straight or branched chain alkyl, which is linked to the structure by oxygen atom. The "haloalkoxy" refers to straight or branched chain alkoxy, in which hydrogen atoms may be all or partly substituted with halogen, such as chloromethoxy, dichloromethoxy, trichloromethoxy, fluoromethoxy, difluoromethoxy, trifluoromethoxy, chlorofluoromethoxy, trifluoroethoxy, etc.

The "alkylthio" refers to straight or branched chain alkyl, which is linked to the structure by sulfur atom. The "haloalkylthio" refers to straight or branched chain alkylthio, in which hydrogen atoms may be all or partly substituted with halogen, such as chloromethylthio, dichloromethylthio, trichloromethylthio, fluoromethylthio, difluoromethylthio, trifluoromethylthio, chlorofluoromethylthio, etc.

The "alkoxyalkyl" means alkoxy is linked to the structure by alkyl. Such as —$CH_2OCH_2$, —$CH_2OCH_2CH_3$.

The "haloalkoxyalkyl" refers to alkoxyalkyl, in which hydrogen atoms may be all or partly substituted with halogen, such as —$CH_2OCH_2CH_2Cl$.

The "alkoxyalkoxy" means OCH$_2$OCH$_2$CH$_3$ etc. The "haloalkoxyalkoxy" means —OCH$_2$OCH$_2$CH$_2$Cl etc.

The "alkylthioalkyl" means alkylthio is linked to the structure by alkyl. Such as —CH$_2$SCH$_2$.

The "haloalkylthioalkyl" means haloalkylthio is linked to the structure by alkyl.

The "alkylamino" refers to straight or branched chain alkyl, which is linked to the structure by nitrogen atom.

The "haloalkylamino" refers to straight or branched chain alkylamino, in which hydrogen atoms may be all or partly substituted with halogen.

The alkenyl refers to straight or branched chain alkenyl, such as ethenyl, 1-propenyl, 2-propenyl and different isomer of butenyl, pentenyl and hexenyl. Alkenyl also includes polyene, such as propa-1,2-dienyl and hexa-2,4-dienyl. The haloalkenyl stands for straight or branched chain alkenyl, in which hydrogen atoms can be all or partly substituted with halogen. The alkynyl refers to straight or branched chain alkynyl, such as ethynyl, 1-propynyl and different isomer of butynyl, pentynyl and hexynyl. Alkynyl also includes groups including more than one triple bonds, such as hexa-2,5-diynyl. The "haloalkynyl" stands for straight or branched chain alkynyl, in which hydrogen atoms can be all or partly substituted with halogen.

The alkenoxyl refers to straight or branched chain alkynes is linked to the structure by oxygen, such as propenyloxy. The haloalkenoxyl stands for a straight-chain or branched alkenoxyl, in which hydrogen atoms may be all or partly substituted with halogen. The alkynoxyl refers to straight or branched chain alkynes is linked to the structure by oxygen, such as propynyloxy. The haloalkynoxyl stands for a straight-chain or branched alkynoxyl, in which hydrogen atoms may be all or partly substituted with halogen.

The "alkylsulfonyl" means a straight-chain or branched alkyl is linked to the structure by (—SO$_2$—), such as methylsulfonyl. The "haloalkylsulfonyl" stands for a straight-chain or branched alkylsulfonyl, in which hydrogen atoms may be all or partly substituted with halogen.

The "alkylsulfinyl" means a straight-chain or branched alkyl is linked to the structure by (—SO—), such as methylsulfinyl.

The "haloalkylsulfinyl" stands for a straight-chain or branched alkylsulfinyl, in which hydrogen atoms may be all or partly substituted with halogen.

The "alkylcarbonyl" means alkyl is linked to the structure by carbonyl. such as CH$_3$CO—, CH$_3$CH$_2$CO—.

The "haloalkylcarbonyl" stands for a straight-chain or branched alkylcarbonyl, in which hydrogen atoms may be all or partly substituted with halogen, such as CF$_3$CO—.

The "alkylcarbonyloxy" means CH$_3$COO—, CH$_3$CH$_2$NHCOO— etc. The "alkylcarbonylamino" means CH$_3$CONH—, CH$_3$CH$_2$NHCONH— etc.

The "alkylsulfonyloxy" means alkyl-S(O)$_2$—O—. The "alkoxycarbonyl" means alkyl-O—CO—.

The "haloalkoxycarbonyl" stands for alkoxycarbonyl, in which hydrogen atoms can be all or partly substituted with halogen, such as —COOCH$_2$CF$_3$, —COOCH$_2$CH$_2$Cl.

The "alkylaminosulfonyl" means —S(O)$_2$NHCH$_3$, —S(O)$_2$NHCH$_2$CH$_3$ etc. The "alkoxycarbonylamino" means —NHCOOCH$_3$, —NHCOOCH$_2$CH$_3$ etc. The "alkoxycarbonylalkyl" means —CH$_2$COOCH$_3$, —CH$_2$COOCH$_2$CH$_3$ etc. The "alkoxycarbonylalkoxy" means —OCH$_2$COOCH$_3$, —OCH$_2$COOCH$_2$CH$_3$ etc. The "aminoalkyl" such as —CH$_2$NH$_2$, —CH$_2$CH$_2$NH$_2$. The "alkylaminoalkyl" such as CH$_2$NHCH$_3$, —CH$_2$NHCH$_2$CH$_3$. The "dialkylaminoalkyl" such as —CH$_2$NH(CH$_3$)$_2$ etc.

The "aryl" in terms of (hetero)aryl, (hetero)aryloxy, (hetero)arylalkoxyalkyl, (hetero)aryloxyalkyl, (hetero)arylcarbonyl, (hetero)aryloxycarbonyl, (hetero)arylaminocarbonyl, (hetero)arylalkyl or (hetero)arylalkoxy include phenyl or naphthyl etc.

The heteroaryl stands for five member ring or six member ring containing one or more N, O, S hetero atoms. Such as pyridinyl, pyrimidinyl, pyrazinyl, pyridazinyl, triazinyl, furyl, thiazolyl, quinolinyl, isothiazolyl, oxazolyl, isoxazolyl, oxadiazolyl, thiadiazolyl, pyrazolyl, pyranyl, triazolyl, tetrazolyl, benzothiazolyl, benzofuranyl, etc. The (hetero)aryloxy such as phenyloxy, pyridinyloxy, pyrimidinyloxy, quinolinyloxy, eye.

The (hetero)arylalkoxyalkyl means —CH$_2$OCH$_2$Ph, 6-chloropyridin-3-ylmethoxyl, etc. The (hetero)aryloxyalkyl means, —CH$_2$OPh, 4,6-(OCH$_3$)$_2$-2-yloxyethyl, etc. The (hetero)arylcarbonyl means PhCHO, 4-ClPhCHO, etc. The (hetero)aryloxycarbonyl means PhOCO, 4-ClPhOCO, 4-NO$_2$PhOCO, Naph OCO, etc. The (hetero)arylaminocarbonyl, (hetero)arylalkyl or (hetero)arylalkoxy includes phenyl or naphthyl etc.

The compounds of the present invention can form stereoisom (Z- and E-isomer respectively) due to the existing of C=C and C=N bonds. The invention includes Z-isomer and E-isomer and their mixture at any ratio.

The drugs were made from the active ingredients of general formula I substituent benzyloxy group containing ether compounds, which can dose by oral medication or parenteral route, also by implantable medication pump and other methods.

The substituent benzyloxy group containing ether compounds having the general formula I in present invention can be used to prepare the drugs for curing or alleviating the cancer. The formulations include tablets, pills, capsule, granule, syrup, injection or freeze-dried powder injection.

Furthermore, the substituent benzyloxy group containing ether compounds having the general formula I in present invention can be used to cure or alleviate the cancer causing by cancer cells of human tissue or organ. The cancers include but not limited to colon cancer, liver cancer, lymph cancer, lung cancer, esophageal cancer, breast cancer, central nervous system cancer, melanoma, ovarian cancer, cervical cancer, renal cancer, leukemia, prostatic cancer, pancreatic cancer, bladder cancer, rectal cancer or stomach cancer.

Part of the substitutes of $R_1$, $R_2$, $R_3$, $R_4$, $R_5$ and $R_6$ in formula I are separately listed in table 1, but without being restricted thereby.

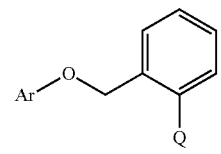

I

TABLE 1 substitute R₁ (R₂, R₃, R₄, R₅, R₆)

| $R_1$ ($R_2$, $R_3$, $R_4$, $R_5$, $R_6$) | $R_1$ ($R_2$, $R_3$, $R_4$, $R_5$, $R_6$) | $R_1$ ($R_2$, $R_3$, $R_4$, $R_5$, $R_6$) | $R_1$ ($R_2$, $R_3$, $R_4$, $R_5$, $R_6$) |
|---|---|---|---|
| H | NH(CH₂)₃CH₃ | OCONHCH₂CH₃ | Ph-2,3-2CN-4,5,6-3Cl |
| F | NHC(CH₃)₃ | OCON(CH₂CH₃)₂ | Ph-2,3-2CN-3,5,6-3Cl |
| Cl | 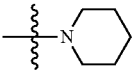 | OCONH(CH₂)₂CH₃ | OPh |
| Br | 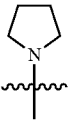 | OCONHCH(CH₃)₂ | CONHPh-2-Cl-4-CF₃ |
| I | 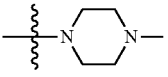 | OCONH(CH₂)₃CH₃ | CONHPh-2-Cl-4-NO₂ |
| CN | 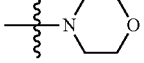 | OCONHC(CH₃)₃ | CH₂Ph |
| NO₂ | CH₂CH=CH₂ | CSNH₂ | CH₂—Ph-4-Cl |
| OH | CH₂CH=CF₂ | CSNHCH₃ | CH₂CH₂Ph |
| NH₂ | CH₂CH₂CH=CF₂ | CSN(CH₃)₂ | CH₂CH₂—Ph-4-Cl |
| CHO | CH₂CH₂CF=CF₂ | CSNHCH₂CH₃ | OCH₂Ph |
| COOH | CH₂CH=CCl₂ | CSN(CH₂CH₃)₂ | OCH₂CH₂Ph |
| CO₂Na | CH₂C≡CH | CSNH(CH₂)₂CH₃ | CH₂OCH₂Ph |
| CO₂NH₄ | CH₂C≡C—I | CSNHCH(CH₃)₂ | CH₂OCH₂CH₂Ph |
| CH₃ | CH₂C≡C—Cl | CSNH(CH₂)₃CH₃ | CH₂OPh |
| CH₂CH₃ | CH₂C≡CCH₃ | CSNHC(CH₃)₃ | naphthyloxy |
| n-C₃H₇ | OCH₂CH=CH₂ | SO₂NH₂ | naphthylmethyl |
| i-C₃H₇ | OCH₂CH=CCl₂ | SO₂NHCH₃ | 6-chloropyridin-3-yl |
| i-C₃H₇CH₂CH₂ | OCH₂C≡CH | SO₂N(CH₃)₂ | 3-Cl-5-CF₃-pyridin-2-yl |
| n-C₄H₉ | SO₂CH₃ | C(=NOCH₃)CH₃ | 5-CF₃-pyridin-2-yl |
| i-C₄H₉ | SO₂CH₂CH₃ | Ph | 3,5,6-Cl₃-pyridin-2-yl |
| n-C₅H₁₁ | SOCH₃ | Ph-2-F | 3,5-Cl₂-pyridin-2-yl |
| n-C₆H₁₃ | SOCH₃CH₃ | Ph-3-F | 5-OCF₃-pyridin-2-yl |
| CH₂Bu-t | COCH₃ | Ph-4-F | 6-Cl-pyridazin-3-yl |
| CF₃ | COCH₂CH₃ | Ph-2-Cl | 6-CF₃-pyridazin-3-yl |
| CHF₂ | COCF₃ | Ph-3-Cl | 6-OCF₃-pyridazin-3-yl |
| CH₂F | COCH₂Cl | Ph-4-Cl | 3-Cl-pyrazin-2-y |
| CH₂Cl | COCH₂CH₂Cl | Ph-4-CH₃ | 6-Cl-pyrazin-2-y |
| CH₂Br | OCOCH₃ | Ph-3-CH₃ | pyrimidin-2-yl |
| CH₂CF₃ | OCOCH₂CH₃ | Ph-2-OCH₃ | pyrimidin-4-yl |
| CF₂CHF₂ | NHCOCH₃ | Ph-3-OCH₃ | pyrimidin-5-yl |
| CF₂CF₃ | NHCOCH₂CH₃ | Ph-4-OCH₃ | 5-Cl-pyrimidin-2-yl |
|  | OSO₂CH₃ | Ph-2-CF₃ | 5-CF₃-pyrimidin-2-yl |
|  | OSO₂CH₂CH₃ | Ph-3-CF₃ | 5-OCH₃—CO-pyridin-2-yl |
|  | CO₂CH₃ | Ph-4-CF₃ | 4,6-(CH₃)₂-pyrimidin-2-yl |
| OCH₃ | CO₂CH₂CH₃ | Ph-2-OCF₃ | 4,6-(OCH₃)₂-pyrimidin-2-yl |
| OCH₂CH₃ | CO₂CH₂CH₂Cl | Ph-3-OCF₃ | 4,6-(CH₃)₂-triazin-2-yl |
| O(CH₂)₂CH₃ | SO₂NH₂ | Ph-4-OCF₃ | 4,6-(OCH₃)₂-triazin-2-yl |
| OCH(CH₃)₂ | SO₂NHCH₃ | Ph-4-NO₂ | 5-Cl-benzoxazol-2-yl |
| OCF₃ | SO₂N(CH₃)₂ | Ph-4-CN | 6-Cl-quinoxalin-2-yl |
| OCH₂CF₃ | NHCOOCH₃ | Ph-4-t-Bu | 4-CH₃-benzyl |
| OCF₂CF₃ | NHCOOCH₂CH₃ | Ph-2,4-2Cl | 2-CN-benzyl |
| SCH₃ | CH₂CO₂CH₃ | Ph-2,4-2F | 2-Cl-6-F-benzyl |
| CH₂OCH₃ | CH₂CO₂CH₂CH₃ | Ph-3,5-2Cl | 2,5-Cl₂-benzyl |
| CH₂OCH₂CH₃ | OCH₂CO₂CH₃ | Ph-3,4-2Cl | 6-Cl-pyridin-3-ylmethyl |
| CH₂OCH₂Cl | CH₂NHCH₃ | Ph-2,3-2Cl | 2-Ck-thiazol-5-ylmethyl |
| CH₂OCH₂CHF₂ | CH₂N(CH₃)₂ | Ph-2,5-2Cl | benzoxazol-2-yloxy |
| CH₂OCH₂CF₃ | CONH₂ | Ph-2,6-2Cl | 5-Cl-benzoxazol-2-ylmethyl |

TABLE 1-continued substitute $R_1$ ($R_2$, $R_3$, $R_4$, $R_5$, $R_6$)

| $R_1$ ($R_2$, $R_3$, $R_4$, $R_5$, $R_6$) | $R_1$ ($R_2$, $R_3$, $R_4$, $R_5$, $R_6$) | $R_1$ ($R_2$, $R_3$, $R_4$, $R_5$, $R_6$) | $R_1$ ($R_2$, $R_3$, $R_4$, $R_5$, $R_6$) |
|---|---|---|---|
| $CH_2SCH_3$ | $CONHCH_3$ | Ph-2-$CH_3$-4-Cl | 3-Cl-5-$CF_3$-pyridin-2-yloxy |
| $CH_2SCH_2CH_3$ | $CON(CH_3)_2$ | Ph-2-Cl-4-$CF_3$ | 6-Cl-pyridn-3-ylmethoxyl |
| $CH_2SCH_2Cl$ | $CONHCH_2CH_3$ | Ph-3,4-$(OMe)_2$ | 2-Cl-thiazol-5-ylmethoxy |
| $CH_2SCH_2CHF_2$ | $CON(CH_2CH_3)_2$ | Ph-2,6-2Cl-4-$CF_3$ | 5-$CH_2$Cl-pyridin-2-yloxymethyl |
| $NHCH_3$ | $CONH(CH_2)_2CH_3$ | Ph-2,6-2Cl-4-$NO_2$ | 6-Cl-pyridin-3-ylmethoxymethyl |
| $N(CH_3)_2$ | $CONHCH(CH_3)_2$ | Ph-2,4,6-3Cl | 6-Cl-pyridn-3-yl(C=O) |
| $NHCH_2CH_3$ | $CONH(CH_2)_3CH_3$ | Ph-2,4,6-3$CH_3$ | pyridn-2-ylO(C=O) |
| $N(CH_2CH_3)_2$ | $CONHC(CH_3)_3$ | Ph-2-$CH_3$-3-Cl-4,6-2$NO_2$ | pyridn-3-yl NH(C=O) |
| $NH(CH_2)_2CH_3$ | $OCONHCH_3$ | Ph-3-Cl-2,6-2$NO_2$-4-$CF_3$ | |
| $NHCH(CH_3)_2$ | $OCON(CH_3)_2$ | Ph-2,5-2CN-3,4,6-3Cl | |
| | | $R_1$, $R_2$ | |
| $CH_2CH_2CH_2$ | $CH_2CH_2CH_2CH_2$ | $CH_2CH_2CH_2CH_2CH_2$ | |

The present invention is also explained by the following compounds having general formula I with antitumor activity in Table 2-Table 53, but without being restricted thereby.

When Ar is Ar1, Q is $Q_1$, the presentitive compounds 2-1 to 2-112 are listed in Table 2.

TABLE 2 substituents when Ar = Ar1

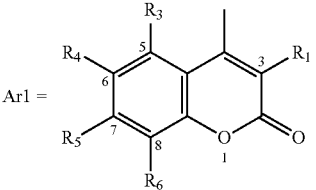

Ar1 =

| No. | $R_1$ | $R_3$ | $R_4$ | $R_5$ | $R_6$ |
|---|---|---|---|---|---|
| 2-1 | H | H | H | H | H |
| 2-2 | $CH_3$ | H | H | H | H |
| 2-3 | $C_2H_5$ | H | H | H | H |
| 2-4 | i-$C_3H_7$ | H | H | H | H |
| 2-5 | n-$C_3H_7$ | H | H | H | H |
| 2-6 | n-$C_4H_9$ | H | H | H | H |
| 2-7 | t-$C_4H_9$ | H | H | H | H |
| 2-8 | $OCH_3$ | H | H | H | H |
| 2-9 | $OC_2H_5$ | H | H | H | H |
| 2-10 | $CH_2Cl$ | H | H | H | H |
| 2-11 | $CH_2NH_2$ | H | H | H | H |
| 2-12 | $CH_2CH_2NH_2$ | H | H | H | H |
| 2-13 | $CH_2CH_2CN$ | H | H | H | H |
| 2-14 | $NH_2$ | H | H | H | H |
| 2-15 | $NO_2$ | H | H | H | H |
| 2-16 | OH | H | H | H | H |
| 2-17 | $CO_2H$ | H | H | H | H |
| 2-18 | F | H | H | H | H |
| 2-19 | Cl | H | H | H | H |
| 2-20 | Br | H | H | H | H |
| 2-21 | I | H | H | H | H |
| 2-22 | $CH_2$—CH=$CH_2$ | H | H | H | H |
| 2-38 | $CH_2$—C≡CH | H | H | H | H |
| 2-39 | H | $CH_3$ | H | H | H |
| 2-40 | H | $C_2H_5$ | H | H | H |
| 2-41 | H | i-$C_3H_7$ | H | H | H |
| 2-42 | H | n-$C_3H_7$ | H | H | H |
| 2-43 | H | n-$C_4H_9$ | H | H | H |
| 2-44 | H | t-$C_4H_9$ | H | H | H |
| 2-45 | H | $OCH_3$ | H | H | H |
| 2-46 | H | $OC_2H_5$ | H | H | H |
| 2-47 | H | $CH_2Cl$ | H | H | H |
| 2-48 | H | $CO_2H$ | H | H | H |
| 2-49 | H | F | H | H | H |
| 2-50 | H | Cl | H | H | H |
| 2-51 | H | Br | H | H | H |
| 2-52 | H | I | H | H | H |
| 2-53 | H | Ph | H | H | H |
| 2-54 | H | H | $CH_3$ | H | H |
| 2-55 | H | H | $C_2H_5$ | H | H |
| 2-56 | H | H | i-$C_3H_7$ | H | H |
| 2-57 | H | H | n-$C_3H_7$ | H | H |
| 2-58 | H | H | n-$C_4H_9$ | H | H |
| 2-59 | H | H | t-$C_4H_9$ | H | H |
| 2-60 | H | H | $OCH_3$ | H | H |
| 2-61 | H | H | $OC_2H_5$ | H | H |
| 2-62 | H | H | $NH_2$ | H | H |
| 2-63 | H | H | OH | H | H |
| 2-64 | H | H | $CO_2H$ | H | H |
| 2-65 | H | H | F | H | H |
| 2-66 | H | H | Cl | H | H |
| 2-67 | H | H | Br | H | H |
| 2-68 | H | H | I | H | H |
| 2-69 | H | H | Ph | H | H |
| 2-70 | H | H | H | $CH_3$ | H |
| 2-71 | H | H | H | $C_2H_5$ | H |
| 2-72 | H | H | H | i-$C_3H_7$ | H |
| 2-73 | H | H | H | n-$C_3H_7$ | H |
| 2-74 | H | H | H | n-$C_4H_9$ | H |
| 2-75 | H7 | H | H | t-$C_4H_9$ | H |
| 2-76 | H | H | H | $OCH_3$ | H |
| 2-77 | H | H | H | $OC_2H_5$ | H |
| 2-78 | H | H | H | $CH_2Cl$ | H |
| 2-79 | H | H | H | $N(CH_3)_2$ | H |
| 2-80 | H | H | H | $OCOOCH_3$ | H |
| 2-81 | H | H | H | $OCOCH_3$ | H |
| 2-82 | H | H | H | $NH_2$ | H |
| 2-83 | H | H | H | CN | H |
| 2-84 | H | H | H | OH | H |
| 2-85 | H | H | H | $CO_2H$ | H |
| 2-86 | H | H | H | F | H |
| 2-87 | H | H | H | Cl | H |
| 2-88 | H | H | H | Br | H |
| 2-89 | H | H | H | I | H |
| 2-90 | H | H | H | $CH_2$—CH=$CH_2$ | H |
| 2-91 | H | H | H | $CH_2$—C≡CH | H |
| 2-92 | H | H | H | H | $CH_3$ |

TABLE 2-continued substituents when Ar = Ar1

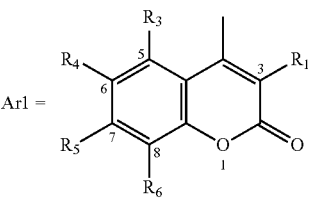

| No. | $R_1$ | $R_3$ | $R_4$ | $R_5$ | $R_6$ |
|---|---|---|---|---|---|
| 2-93 | H | H | H | H | $C_2H_5$ |
| 2-94 | H | H | H | H | $OCH_3$ |
| 2-95 | H | H | H | H | CHO |
| 2-96 | H | H | H | H | F |
| 2-97 | H | H | H | H | Cl |
| 2-98 | H | H | H | H | Br |
| 2-99 | H | H | H | H | I |
| 2-100 | H | H | H | H | Ph |
| 2-101 | H | H | H | H | $CH_2Ph$ |
| 2-102 | $CH_3$ | H | H | H | $CH_3$ |
| 2-103 | H | H | $CH_3$ | $CH_3$ | H |
| 2-104 | H | H | $CH_3$ | H | $CH_3$ |
| 2-105 | H | H | $OCH_3$ | H | $OCH_3$ |
| 2-106 | H | H | Cl | H | Cl |
| 2-107 | H | H | H | $CH_3$ | $CH_3$ |
| 2-108 | $CH_3$ | H | H | $CH_3$ | H |
| 2-109 | H | H | Cl | $CH_3$ | H |
| 2-110 | H | H | $C_2H_5$ | $C_2H_5$ | H |
| 2-111 | $CH_3$ | H | $CH_3$ | H | H |
| 2-112 | H | $CH_3$ | $CH_3$ | H | $CH_3$ |

Table 3: When Ar is Ar1, Q is $Q_2$, the substituents of presentitive compounds 3-1 to 3-112 are consistent with 2-1 to 2-112 in Table 2;

Table 4: When Ar is Ar1, Q is $Q_3$, the substituents of presentitive compounds 4-1 to 4-112 are consistent with 2-1 to 2-112 in Table 2;

Table 5: When Ar is Ar1, Q is $Q_4$, the substituents of presentitive compounds 5-1 to 5-112 are consistent with 2-1 to 2-112 in Table 2;

Table 6: When Ar is Ar1, Q is $Q_5$, the substituents of presentitive compounds 6-1 to 6-112 are consistent with 2-1 to 2-112 in Table 2;

Table 7: When Ar is Ar1, Q is $Q_6$, the substituents of presentitive compounds 7-1 to 7-112 are consistent with 2-1 to 2-112 in Table 2;

Table 8: When Ar is Ar1, Q is $Q_7$, the substituents of presentitive compounds 8-1 to 8-112 are consistent with 2-1 to 2-112 in Table 2;

Table 9: When Ar is Ar1, Q is $Q_8$ is the substituents of presentitive compounds 9-1 to 9-112 are consistent with 2-1 to 2-112 in Table 2;

Table 10: When Ar is Ar1, Q is $Q_9$, the substituents of presentitive compounds 10-1 to 10-112 are consistent with 2-1 to 2-112 in Table 2;

Table 11: When Ar is Ar1, Q is $Q_{19}$, the substituents of presentitive compounds 11-1 to 11-112 are consistent with 2-1 to 2-112 in Table 2;

Table 12: When Ar is Ar1, Q is $Q_{20}$, the substituents of presentitive compounds 12-1 to 12-112 are consistent with 2-1 to 2-112 in Table 2;

Table 13: When Ar is Ar1, Q is $Q_{21}$, the substituents of presentitive compounds 13-1 to 13-112 are consistent with 2-1 to 2-112 in Table 2;

Table 14: When Ar is Ar1, Q is $Q_{22}$, the substituents of presentitive compounds 14-1 to 14-112 are consistent with 2-1 to 2-112 in Table 2.

When Ar is Ar2, Q is $Q_1$, the presentitive compounds 15-1 to 15-121 are listed in Table 15.

TABLE 15 substituents when Ar = Ar2

| No. | $R_1$ | $R_2$ | $R_3$ | $R_5$ | $R_6$ |
|---|---|---|---|---|---|
| 15-1 | H | H | H | H | H |
| 15-2 | $CH_3$ | H | H | H | H |
| 15-3 | $C_2H_5$ | H | H | H | H |
| 15-4 | $i\text{-}C_3H_7$ | H | H | H | H |
| 15-5 | $n\text{-}C_3H_7$ | H | H | H | H |
| 15-6 | $n\text{-}C_4H_9$ | H | H | H | H |
| 15-7 | $t\text{-}C_4H_9$ | H | H | H | H |
| 15-8 | OH | H | H | H | H |
| 15-9 | $NH_2$ | H | H | H | H |
| 15-10 | CN | H | H | H | H |
| 15-11 | $NO_2$ | H | H | H | H |
| 15-12 | CHO | H | H | H | H |
| 15-13 | $CO_2H$ | H | H | H | H |
| 15-14 | $COCH_3$ | H | H | H | H |
| 15-15 | $CONH_2$ | H | H | H | H |
| 15-16 | $COOCH_3$ | H | H | H | H |
| 15-17 | $CH_2COCH_3$ | H | H | H | H |
| 15-18 | $CH_2\text{—}CH\text{=}CH_2$ | H | H | H | H |
| 15-19 | $C(CH_3)_2\text{—}CH\text{=}CH_2$ | H | H | H | H |
| 15-20 | 4-Cl—Ph | H | H | H | H |
| 15-21 | 4-$CH_3$—Ph | H | H | H | H |
| 15-22 | H | $CH_3$ | H | H | H |

TABLE 15-continued substituents when Ar = Ar2

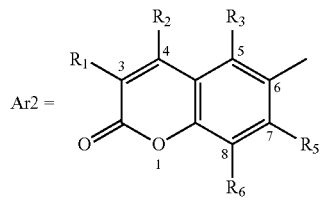

Ar2 =

| No. | $R_1$ | $R_2$ | $R_3$ | $R_5$ | $R_6$ |
|---|---|---|---|---|---|
| 15-23 | H | $C_2H_5$ | H | H | H |
| 15-24 | H | $i$-$C_3H_7$ | H | H | H |
| 15-25 | H | $n$-$C_3H_7$ | H | H | H |
| 15-26 | H | $n$-$C_4H_9$ | H | H | H |
| 15-27 | H | $t$-$C_4H_9$ | H | H | H |
| 15-28 | H | $OCH_3$ | H | H | H |
| 15-29 | H | $OC_2H_5$ | H | H | H |
| 15-30 | H | $CH_2Cl$ | H | H | H |
| 15-31 | H | $CH_2NH_2$ | H | H | H |
| 15-32 | H | $CH_2CH_2NH_2$ | H | H | H |
| 15-33 | H | $COOCH_3$ | H | H | H |
| 15-34 | H | $COCH_3$ | H | H | H |
| 15-35 | H | $CH_2COCH_3$ | H | H | H |
| 15-36 | H | OH | H | H | H |
| 15-37 | H | 4-$t$-$C_4H_9$—Ph | H | H | H |
| 15-38 | H | 4-Cl—Ph | H | H | H |
| 15-39 | H | 4-$CH_3$—Ph | H | H | H |
| 15-40 | H | H | $CH_3$ | H | H |
| 15-41 | H | H | $C_2H_5$ | H | H |
| 15-42 | H | H | $i$-$C_3H_7$ | H | H |
| 15-43 | H | H | $n$-$C_3H_7$ | H | H |
| 15-44 | H | H | $n$-$C_4H_9$ | H | H |
| 15-45 | H | H | $t$-$C_4H_9$ | H | H |
| 15-46 | H | H | OH | H | H |
| 15-47 | H | H | $NH_2$ | H | H |
| 15-48 | H | H | CN | H | H |
| 15-49 | H | H | $NO_2$ | H | H |
| 15-50 | H | H | CHO | H | H |
| 15-51 | H | H | $CO_2H$ | H | H |
| 15-52 | H | H | $COCH_3$ | H | H |
| 15-53 | H | H | $CH_2N(CH_3)_2$ | H | H |
| 15-54 | H | H | $CH_2$—$CH$=$CH_2$ | H | H |
| 15-55 | H | H | $C(CH_3)_2$—$CH$=$CH_2$ | H | H |
| 15-56 | H | H | F | H | H |
| 15-57 | H | H | Cl | H | H |
| 15-58 | H | H | Br | H | H |
| 15-59 | H | H | I | H | H |
| 15-60 | H | H | H | $CH_3$ | H |
| 15-61 | H | H | H | $C_2H_5$ | H |
| 15-62 | H | H | H | $i$-$C_3H_7$ | H |
| 15-63 | H | H | H | $n$-$C_3H_7$ | H |
| 15-64 | H | H | H | $n$-$C_4H_9$ | H |
| 15-65 | H | H | H | $t$-$C_4H_9$ | H |
| 15-66 | H | H | H | $OCH_3$ | H |
| 15-67 | H | H | H | $OC_2H_5$ | H |
| 15-68 | H | H | H | $CH_2Cl$ | H |
| 15-69 | H | H | H | $COCH_3$ | H |
| 15-70 | H | H | H | $NH_2$ | H |
| 15-71 | H | H | H | $NO_2$ | H |
| 15-72 | H | H | H | OH | H |
| 15-73 | H | H | H | $OCOCH_3$ | H |
| 15-74 | H | H | H | F | H |
| 15-75 | H | H | H | Cl | H |
| 15-76 | H | H | H | Br | H |
| 15-77 | H | H | H | I | H |
| 15-78 | H | H | H | $CH_2$—$CH$=$CH_2$ | H |
| 15-79 | H | H | H | $CH_2$—$C$≡$CH$ | H |
| 15-80 | H | H | H | H | $CH_3$ |
| 15-81 | H | H | H | H | $C_2H_5$ |
| 15-82 | H | H | H | H | $i$-$C_3H_7$ |
| 15-83 | H | H | H | H | $n$-$C_3H_7$ |
| 15-84 | H | H | H | H | $n$-$C_4H_9$ |
| 15-85 | H | H | H | H | $t$-$C_4H_9$ |
| 15-86 | H | H | H | H | $OCH_3$ |
| 15-87 | H | H | H | H | $OC_2H_5$ |
| 15-88 | H | H | H | H | OH |

TABLE 15-continued substituents when Ar = Ar2

$$Ar2 = \text{(chromen-2-one structure with positions: } R_1 \text{ at 3, } R_2 \text{ at 4, } R_3 \text{ at 5, CH}_3 \text{ at 6, } R_5 \text{ at 7, } R_6 \text{ at 8)}$$

| No. | $R_1$ | $R_2$ | $R_3$ | $R_5$ | $R_6$ |
|---|---|---|---|---|---|
| 15-89 | H | H | H | H | $C(NOCH_3)CH_3$ |
| 15-90 | H | H | H | H | F |
| 15-91 | H | H | H | H | Cl |
| 15-92 | H | H | H | H | Br |
| 15-93 | H | H | H | H | I |
| 15-94 | H | H | H | H | $CH_2$—$CH$=$C(CH_3)_2$ |
| 15-95 | H | $CH_3$ | H | H | $CH_3$ |
| 15-96 | H | Ph | H | H | $CH_3$ |
| 15-97 | H | Ph | H | H | $OCH_3$ |
| 15-98 | H | $CH_2Cl$ | H | H | Ph |
| 15-99 | H | H | $CH_3$ | H | $CH_3$ |
| 15-100 | H | H | $OCH_3$ | H | $OCH_3$ |
| 15-101 | $CH_3$ | H | H | $OCH_3$ | H |
| 15-102 | $CH_3$ | H | H | $CH$=$CH_2Ph$ | H |
| 15-103 | H | $CH_3$ | $CH_3$ | H | H |
| 15-104 | $CH_3$ | $CH_3$ | H | H | H |
| 15-105 | Ph | $CH_3$ | H | H | H |
| 15-106 | H | $CH_3$ | $OCH_3$ | H | H |
| 15-107 | H | $CH_3$ | Cl | H | H |
| 15-108 | H | $CH_3$ | H | H | $t$-$C_4H_9$ |
| 15-109 | H | H | H | $OCH_3$ | $OCH_3$ |
| 15-110 | H | H | $CH_3$ | $CH_3$ | $CH_3$ |
| 15-111 | H | $CH_3$ | H | $CH_3$ | $CH_3$ |
| 15-112 | $CH_3$ | $CH_3$ | H | $CH_3$ | H |
| 15-113 | H | H | $OCH_3$ | $OCH_3$ | $OCH_3$ |
| 15-114 | $CH_2CH_2CH_2$ | | H | H | H |
| 15-115 | $CH_2CH_2CH_2$ | | H | H | $CH_3$ |
| 15-116 | $CH_2CH_2CH_2$ | | H | $CH_3$ | H |
| 15-117 | $CH_2CH_2CH_2$ | | H | Ph | H |
| 15-118 | $CH_2CH_2CH_2CH_2$ | | H | H | H |
| 15-119 | $CH_2CH_2CH_2CH_2$ | | H | H | $CH_3$ |
| 15-120 | $CH_2CH_2CH_2CH_2$ | | H | $CH_3$ | H |
| 15-121 | $CH_2CH_2CH_2CH_2$ | | H | Ph | H |

Table 16: When Ar is Ar2, Q is $Q_2$, the substituents of presentitive compounds 16-1 to 16-121 are consistent with 15-1 to 15-121 in Table 15;

Table 17: When Ar is Ar2, Q is $Q_3$, the substituents of presentitive compounds 17-1 to 17-121 are consistent with 15-1 to 15-121 in Table 15;

Table 18: When Ar is Ar2, Q is $Q_4$, the substituents of presentitive compounds 18-1 to 18-121 are consistent with 15-1 to 15-121 in Table 15;

Table 19: When Ar is Ar2, Q is $Q_5$, the substituents of presentitive compounds 19-1 to 19-121 are consistent with 15-1 to 15-121 in Table 15;

Table 20: When Ar is Ar2, Q is $Q_6$, the substituents of presentitive compounds 20-1 to 20-121 are consistent with 15-1 to 15-121 in Table 15;

Table 21: When Ar is Ar2, Q is $Q_7$, the substituents of presentitive compounds 21-1 to 21-121 are consistent with 15-1 to 15-121 in Table 15;

Table 22: When Ar is Ar2, Q is $Q_8$, the substituents of presentitive compounds 22-1 to 22-121 are consistent with 15-1 to 15-121 in Table 15;

Table 23: When Ar is Ar2, Q is $Q_9$, the substituents of presentitive compounds 23-1 to 23-121 are consistent with 15-1 to 15-121 in Table 15;

Table 24: When Ar is Ar2, Q is $Q_{19}$, the substituents of presentitive compounds 24-1 to 24-121 are consistent with 15-1 to 15-121 in Table 15;

Table 25: When Ar is Ar2, Q is $Q_{20}$, the substituents of presentitive compounds 25-1 to 25-121 are consistent with 15-1 to 15-121 in Table 15;

Table 26: When Ar is Ar2, Q is $Q_{21}$, the substituents of presentitive compounds 26-1 to 26-121 are consistent with 15-1 to 15-121 in Table 15;

Table 27: When Ar is Ar2, Q is $Q_{22}$, the substituents of presentitive compounds 27-1 to 27-121 are consistent with 15-1 to 15-121 in Table 15;

When Ar is Ar3, Q is $Q_1$, the presentitive compounds 28-1 to 28-139 are listed in Table 28.

TABLE 28 substituents when Ar = Ar3

Ar3 = [coumarin structure with R1 at position 3, R2 at position 4, R3 at position 5, R4 at position 6, methyl at position 7, R6 at position 8]

| NO. | R₁ | R₂ | R₄ | R₆ |
|---|---|---|---|---|
| 28-1 | H | H | H | H |
| 28-2 | H | CH₃ | H | H |
| 28-3 | H | CH₃ | H | CH₃ |
| 28-4 | H | Ph | H | CH₃ |
| 28-5 | CH₃ | CH₃ | H | H |
| 28-6 | CH₃ | CH₃ | H | CH₃ |
| 28-7 | H | CF₃ | H | H |
| 28-8 | H | CH₃ | H | E |
| 28-9 | H | CH₃ | E | H |
| 28-10 | H | CH₃ | COCH₃ | H |
| 28-11 | H | CH₃ | H | COCH₃ |
| 28-12 | Cl | CH₃ | H | H |
| 28-13 | H | CH₂Cl | H | H |
| 28-14 | Cl | CH₂Cl | H | H |
| 28-15 | Cl | CH₂OCH₃ | H | H |
| 28-16 | Cl | CH₂CH₃ | H | H |
| 28-17 | H | CH₂CH₃ | H | CH₃ |
| 28-18 | C₂H₅ | CH₃ | H | H |
| 28-19 | H | CH₂OCH₃ | H | H |
| 28-20 | H | CH₂OC₂H₅ | H | H |
| 28-21 | Cl | CH₂OC₂H₅ | H | H |
| 28-22 | OCH₃ | CH₂OCH₃ | H | H |
| 28-23 | N(CH₃)₂ | CH₃ | H | H |
| 28-24 | CN | H | H | H |
| 28-25 | Cl | CH₃ | H | CH₃ |
| 28-26 | H | CH(CH₃)₂ | H | H |
| 28-27 | C₃H₇ | CH₃ | H | H |
| 28-28 | H | t C₄H₉ | H | H |
| 28-29 | H | 4-Cl—Ph | H | H |
| 28-30 | Cl | 4-Cl—Ph | H | H |
| 28-31 | H | 4-Cl—Ph | H | CH₃ |
| 28-32 | Cl | Ph | H | H |
| 28-33 | H | CH₂CH₃ | H | H |
| 28-34 | H | CH₂C₂H₅ | H | H |
| 28-35 | H | CH₂C₂H₅ | H | CH₃ |
| 28-36 | Cl | CH₂C₂H₅ | H | H |
| 28-37 | CH₃ | CH₂C₂H₅ | H | H |
| 28-38 | H | 4-F—Ph | H | H |
| 28-39 | Cl | 4-F—Ph | H | H |
| 28-40 | H | 4-F—Ph | H | CH₃ |
| 28-41 | H | 4-CF₃—Ph | H | H |
| 28-42 | Cl | 4-CF₃—Ph | H | H |
| 28-43 | Cl | CH₂N(CH₃)₂ | H | H |
| 28-44 | OCH₃ | C₂H₅ | H | H |
| 28-45 | OCH₃ | CH₃ | H | H |
| 28-46 | OC₂H₅ | CH₃ | H | H |
| 28-47 | H | CH₂OCH₂CF₃ | H | H |
| 28-48 | Cl | CH₂OCH₂CF₃ | H | H |
| 28-49 | F | CF₃ | H | H |
| 28-50 | F | CH₃ | H | H |
| 28-51 | H | CH₂N(CH₃)₂ | H | H |
| 28-52 | H | Ph | H | H |
| 28-53 | Cl | Cl | H | H |
| 28-54 | F | Cl | H | H |
| 28-55 | H | CH₂OCH₂Ph | E | H |
| 28-56 | OCH₃ | 4-Cl—Ph | H | H |
| 28-57 | F | 4-Cl—Ph | H | H |
| 28-58 | H | M | H | H |
| 28-59 | Cl | M | H | H |
| 28-60 | Cl | M | H | CH₃ |
| 28-61 | CH₂S | CH₃ | H | H |
| 28-62 | CH₃SO₂ | CH₃ | H | H |
| 28-63 | F | F | H | H |
| 28-64 | CH₃SO₂ | Cl | H | H |
| 28-65 | H | 4-NO₂—Ph | H | H |
| 28-66 | Cl | 4-NO₂—Ph | H | H |
| 28-67 | H | 4-NO₂—Ph | H | CH₃ |
| 28-68 | PhCH₂ | CH₃ | H | H |
| 28-69 | PhCH₂ | CH₃ | H | CH₃ |
| 28-70 | CF₃CH₂O | C₃H₇ | H | H |
| 28-71 | i-C₃H₇ | CH₃ | H | H |
| 28-72 | n-C₆H₁₃ | CH₃ | H | H |
| 28-73 | n-C₅H₁₁ | CH₃ | H | H |
| 28-74 | C₂H₄—i-Pr | CH₃ | H | H |
| 28-75 | n-C₆H₁₃ | CH₃ | H | H |
| 28-76 | H | n-C₄H₉ | H | H |
| 28-77 | H | n-C₅H₁₁ | H | H |
| 28-78 | H | CH(CH₃)₂ | H | CH₃ |
| 28-79 | n-C₃H₇ | n-C₃H₇ | H | H |
| 28-80 | CH₃ | n-C₄H₉ | H | H |
| 28-81 | C₂H₅ | n-C₄H₉ | H | H |
| 28-82 | C₃H₇ | n-C₄H₉ | H | H |
| 28-83 | i-C₃H₇ | n-C₄H₉ | H | H |
| 28-84 | n-C₄H₉ | n-C₄H₉ | H | H |
| 28-85 | CH₃ | n-C₅H₁₁ | H | H |
| 28-86 | C₂H₅ | n-C₅H₁₁ | H | H |
| 28-87 | C₃H₇ | n-C₅H₁₁ | H | H |
| 28-88 | i-C₃H₇ | n-C₅H₁₁ | H | H |
| 28-89 | n-C₄H₉ | n-C₅H₁₁ | H | H |
| 28-90 | H | n-C₆H₁₃ | H | H |
| 28-91 | CH₃ | n-C₆H₁₃ | H | H |
| 28-92 | C₂H₅ | n-C₆H₁₃ | H | H |
| 28-93 | C₃H₇ | n-C₆H₁₃ | H | H |
| 28-94 | i-C₃H₇ | n-C₆H₁₃ | H | H |
| 28-95 | n-C₄H₉ | n-C₆H₁₃ | H | H |
| 28-96 | H | CH₂—Ph-4-Cl | H | H |
| 28-97 | CH₃ | CH₂—Ph-4-Cl | H | H |
| 28-98 | C₂H₅ | CH₂—Ph-4-Cl | H | H |
| 28-99 | CH₂—Ph-4-Cl | CH₃ | H | H |
| 28-100 | CH₂—Ph-4-Cl | C₂H₅ | H | H |
| 28-101 | CH₂—Ph-4-Cl | C₃H₇ | H | H |
| 28-102 | CH₃ | CF₃ | H | H |
| 28-103 | Cl | CF₃ | H | H |
| 28-104 | C₂H₅ | CF₃ | H | H |
| 28-105 | n-C₃H₇ | CF₃ | H | H |
| 28-106 | n-C₄H₉ | CF₃ | H | H |
| 28-107 | H | CH₂CH₂—Ph-4-Cl | H | H |
| 28-108 | CH₃ | CH₂CH₂—Ph-4-Cl | H | H |
| 28-109 | H | CH₂Bu-t | H | H |
| 28-110 | CH₃ | CH₂Bu-t | H | H |
| 28-111 | n-C₃H₇ | CH₂Bu-t | H | H |
| 28-112 | CH₂Bu-t | CH₃ | H | H |
| 28-113 | CH₂CH₂—Ph-4-Cl | CH₃ | H | H |
| 28-114 | CH₂CH₂—Ph-4-Cl | C₂H₅ | H | H |
| 28-115 | CH₂CH₂—Ph-4-Cl | C₃H₇ | H | H |
| 28-116 | CO₂CH₃ | CH₃ | H | H |
| 28-117 | CO₂CH₃ | CF₃ | H | H |
| 28-118 | CO₂C₂H₅ | C₂H₅ | H | H |
| 28-119 | CO₂C₂H₅ | n-C₃H₇ | H | H |
| 28-120 | CONHCH₃ | CH₃ | H | H |
| 28-121 | CONHC₂H₅ | CH₃ | H | H |
| 28-122 | CON(CH₃)₂ | CH₃ | H | H |
| 28-123 | CH₃ | CO₂CH₃ | H | H |
| 28-124 | H | 6-Cl—Py-3-yl | H | H |
| 28-125 | CH₂CH₂CH₂ | | H | H |
| 28-126 | CH₂CH₂CH₂ | | H | CH₃ |
| 28-127 | CH₂CH₂CH₂ | | CH₃ | H |
| 28-128 | CH₂CH₂CH₂CH₂ | | H | H |
| 28-129 | CH₂CH₂CH₂CH₂ | | H | CH₃ |
| 28-130 | CH₂CH₂CH₂CH₂ | | CH₃ | H |

TABLE 28-continued substituents when Ar = Ar3

Ar3 = [coumarin structure with R6 at position 8, R4 at position 6, R3 at position 5, R2 at position 4, R1 at position 3]

| NO. | R$_1$ | R$_2$ | R$_4$ | R$_6$ |
|---|---|---|---|---|
| 28-131 | CH$_2$CH$_2$CH$_2$CH$_2$ | | Ph | H |
| 28-132 | H | 2-Cl—Ph | H | H |
| 28-133 | H | 3-Cl—Ph | H | H |
| 28-134 | H | 4-Br—Ph | H | H |
| 28-135 | H | 4-CN—Ph | H | H |
| 28-136 | H | 4-CH$_3$—Ph | H | H |
| 28-137 | H | 4-OCH$_3$—Ph | H | H |
| 28-138 | H | 4-OCF$_3$—Ph | H | H |
| 28-139 | H | 4-OCH$_2$CF$_3$—Ph | H | H |

Note:
E is C(CH$_3$)═NOCH$_3$;
M is C$_6$H$_3$-3,4-(OCH$_3$)$_2$.

Table 29: When Ar is Ar3, Q is Q$_2$, the substituents of presentitive compounds 29-1 to 29-131 are consistent with 28-1 to 28-139 in Table 28;

Table 30: When Ar is Ar3, Q is Q$_3$, the substituents of presentitive compounds 30-1 to 30-131 are consistent with 28-1 to 28-139 in Table 28;

Table 31: When Ar is Ar3, Q is Q$_4$, the substituents of presentitive compounds 31-1 to 31-131 are consistent with 28-1 to 28-139 in Table 28;

Table 32: When Ar is Ar3, Q is Q$_5$, the substituents of presentitive compounds 32-1 to 32-131 are consistent with 28-1 to 28-139 in Table 28;

Table 33: When Ar is Ar3, Q is Q$_6$, the substituents of presentitive compounds 33-1 to 33-131 are consistent with 28-1 to 28-139 in Table 28;

Table 34: When Ar is Ar3, Q is Q$_7$, the substituents of presentitive compounds 34-1 to 34-131 are consistent with 28-1 to 28-139 in Table 28;

Table 35: When Ar is Ar3, Q is Q$_8$, the substituents of presentitive compounds 35-1 to 35-131 are consistent with 28-1 to 28-139 in Table 28;

Table 36: When Ar is Ar3, Q is Q$_9$, the substituents of presentitive compounds 36-1 to 36-131 are consistent with 28-1 to 28-139 in Table 28;

Table 37: When Ar is Ar3, Q is Q$_{19}$, the substituents of presentitive compounds 37-1 to 37-131 are consistent with 28-1 to 28-139 in Table 28;

Table 38: When Ar is Ar3, Q is Q$_{20}$, the substituents of presentitive compounds 38-1 to 38-131 are consistent with 28-1 to 28-139 in Table 28;

Table 39: When Ar is Ar3, Q is Q$_{21}$, the substituents of presentitive compounds 39-1 to 39-131 are consistent with 28-1 to 28-139 in Table 28;

Table 40: When Ar is Ar3, Q is Q$_{22}$, the substituents of presentitive compounds 40-1 to 40-131 are consistent with 28-1 to 28-139 in Table 28.

When Ar is Ar4, Q is Q$_1$, the presentitive compounds 41-1 to 41-116 are listed in Table 41.

TABLE 41 substituents when Ar = Ar4

Ar4 = [coumarin structure with CH$_3$ at position 1, R5 at position 7, R4 at position 6, R3 at position 5, R2 at position 4, R1 at position 3]

| No. | R$_1$ | R$_2$ | R$_3$ | R$_4$ | R$_5$ |
|---|---|---|---|---|---|
| 41-1 | H | H | H | H | H |
| 41-2 | CH$_3$ | H | H | H | H |
| 41-3 | C$_2$H$_5$ | H | H | H | H |
| 41-4 | i-C$_3$H$_7$ | H | H | H | H |
| 41-5 | n-C$_3$H$_7$ | H | H | H | H |
| 41-6 | n-C$_4$H$_9$ | H | H | H | H |
| 41-7 | t-C$_4$H$_9$ | H | H | H | H |
| 41-8 | OH | H | H | H | H |
| 41-9 | NH$_2$ | H | H | H | H |
| 41-10 | CN | H | H | H | H |
| 41-11 | NO$_2$ | H | H | H | H |
| 41-12 | CHO | H | H | H | H |
| 41-13 | CO$_2$H | H | H | H | H |
| 41-14 | COCH$_3$ | H | H | H | H |
| 41-15 | CONH$_2$ | H | H | H | H |
| 41-16 | COOCH$_3$ | H | H | H | H |
| 41-17 | CH$_2$COCH$_3$ | H | H | H | H |
| 41-18 | CH$_2$—CH═CH$_2$ | H | H | H | H |
| 41-19 | C(CH$_3$)$_2$—CH═CH$_2$ | H | H | H | H |
| 41-20 | 4-Cl—Ph | H | H | H | H |
| 41-21 | 4-CH$_3$—Ph | H | H | H | H |
| 41-22 | H | CH$_3$ | H | H | H |
| 41-23 | H | C$_2$H$_5$ | H | H | H |
| 41-24 | H | i-C$_3$H$_7$ | H | H | H |
| 41-25 | H | n-C$_3$H$_7$ | H | H | H |
| 41-26 | H | n-C$_4$H$_9$ | H | H | H |

TABLE 41-continued substituents when Ar = Ar4

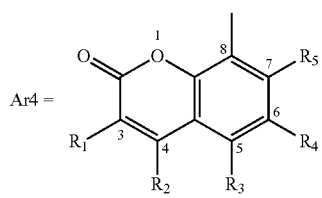

Ar4 =

| No. | $R_1$ | $R_2$ | $R_3$ | $R_4$ | $R_5$ |
|---|---|---|---|---|---|
| 41-27 | H | t-$C_4H_9$ | H | H | H |
| 41-28 | H | $OCH_3$ | H | H | H |
| 41-29 | H | $OC_2H_5$ | H | H | H |
| 41-30 | H | $CH_2Cl$ | H | H | H |
| 41-31 | H | $CH_2NH_2$ | H | H | H |
| 41-32 | H | $CH_2CH_2NH_2$ | H | H | H |
| 41-33 | H | $COOCH_3$ | H | H | H |
| 41-34 | H | $COCH_3$ | H | H | H |
| 41-35 | H | $CH_2COCH_3$ | H | H | H |
| 41-36 | H | OH | H | H | H |
| 41-37 | H | 4-t-$C_4H_9$—Ph | H | H | H |
| 41-38 | H | 4-Cl—Ph | H | H | H |
| 41-39 | H | 4-$CH_3$—Ph | H | H | H |
| 41-40 | H | H | $CH_3$ | H | H |
| 41-41 | H | H | $C_2H_5$ | H | H |
| 41-42 | H | H | i-$C_3H_7$ | H | H |
| 41-43 | H | H | n-$C_3H_7$ | H | H |
| 41-44 | H | H | n-$C_4H_9$ | H | H |
| 41-45 | H | H | t-$C_4H_9$ | H | H |
| 41-46 | H | H | OH | H | H |
| 41-47 | H | H | $NH_2$ | H | H |
| 41-48 | H | H | CN | H | H |
| 41-49 | H | H | $NO_2$ | H | H |
| 41-50 | H | H | CHO | H | H |
| 41-51 | H | H | $CO_2H$ | H | H |
| 41-52 | H | H | $COCH_3$ | H | H |
| 41-53 | H | H | $CH_2N(CH_3)_2$ | H | H |
| 41-54 | H | H | $CH_2$—CH=$CH_2$ | H | H |
| 41-55 | H | H | $C(CH_3)_2$—CH=$CH_2$ | H | H |
| 41-56 | H | H | F | H | H |
| 41-57 | H | H | Cl | H | H |
| 41-58 | H | H | Br | H | H |
| 41-59 | H | H | I | H | H |
| 41-60 | H | H | H | $CH_3$ | H |
| 41-61 | H | H | H | $C_2H_5$ | H |
| 41-62 | H | H | H | i-$C_3H_7$ | H |
| 41-63 | H | H | H | n-$C_3H_7$ | H |
| 41-64 | H | H | H | n-$C_4H_9$ | H |
| 41-65 | H | H | H | t-$C_4H_9$ | H |
| 41-66 | H | H | H | $OCH_3$ | H |
| 41-67 | H | H | H | $OC_2H_5$ | H |
| 41-68 | H | H | H | $CH_2Cl$ | H |
| 41-69 | H | H | H | $COCH_3$ | H |
| 41-70 | H | H | H | $NH_2$ | H |
| 41-71 | H | H | H | $NO_2$ | H |
| 41-72 | H | H | H | OH | H |
| 41-73 | H | H | H | $OCOCH_3$ | H |
| 41-74 | H | H | H | F | H |
| 41-75 | H | H | H | Cl | H |
| 41-76 | H | H | H | Br | H |
| 41-77 | H | H | H | I | H |
| 41-78 | H | H | H | $CH_2$—CH=$CH_2$ | H |
| 41-79 | H | H | H | $CH_2$—C≡CH | H |
| 41-80 | H | H | H | H | $CH_3$ |
| 41-81 | H | H | H | H | $C_2H_5$ |
| 41-82 | H | H | H | H | i-$C_3H_7$ |
| 41-83 | H | H | H | H | n-$C_3H_7$ |
| 41-84 | H | H | H | H | n-$C_4H_9$ |
| 41-85 | H | H | H | H | t-$C_4H_9$ |
| 41-86 | H | H | H | H | $OCH_3$ |
| 41-87 | H | H | H | H | $OC_2H_5$ |
| 41-88 | H | H | H | H | OH |
| 41-89 | H | H | H | H | $C(NOCH_3)CH_3$ |
| 41-90 | H | H | H | H | F |
| 41-91 | H | H | H | H | Cl |
| 41-92 | H | H | H | H | Br |

TABLE 41-continued substituents when Ar = Ar4

$$Ar4 = \begin{array}{c} \text{coumarin structure with positions } 1\text{-}8, \text{ with } R_1 \text{ at 3, } R_2 \text{ at 4, } R_3 \text{ at 5, } R_4 \text{ at 6, } R_5 \text{ at 7} \end{array}$$

| No. | $R_1$ | $R_2$ | $R_3$ | $R_4$ | $R_5$ |
|---|---|---|---|---|---|
| 41-93 | H | H | H | H | I |
| 41-94 | H | H | H | H | $CH_2$—$CH$=$C(CH_3)_2$ |
| 41-95 | H | $CH_3$ | H | H | $CH_3$ |
| 41-96 | H | Ph | H | H | $CH_3$ |
| 41-97 | H | Ph | H | H | $OCH_3$ |
| 41-98 | H | $CH_2Cl$ | H | H | Ph |
| 41-99 | H | H | $CH_3$ | H | $CH_3$ |
| 41-100 | H | H | $OCH_3$ | H | $OCH_3$ |
| 41-101 | $CH_3$ | H | H | $OCH_3$ | H |
| 41-102 | $CH_3$ | H | H | $CH$=$CH_2Ph$ | H |
| 41-103 | H | $CH_3$ | $CH_3$ | H | H |
| 41-104 | $CH_3$ | $CH_3$ | H | H | H |
| 41-105 | Ph | $CH_3$ | H | H | H |
| 41-106 | H | H | $OCH_3$ | H | $OCH_3$ |
| 41-107 | H | $CH_3$ | Cl | H | H |
| 41-108 | H | $CH_3$ | H | H | $CH_3$ |
| 41-109 | H | H | H | $OCH_3$ | $OCH_3$ |
| 41-110 | H | $CH_3$ | $CH_3$ | H | $OCH_3$ |
| 41-111 | $CH_2CH_2CH_2$ | | H | H | H |
| 41-112 | $CH_2CH_2CH_2$ | | H | H | $CH_3$ |
| 41-113 | $CH_2CH_2CH_2$ | | H | H | $OCH_3$ |
| 41-114 | $CH_2CH_2CH_2CH_2$ | | H | H | H |
| 41-115 | $CH_2CH_2CH_2CH_2$ | | H | H | $CH_3$ |
| 41-116 | $CH_2CH_2CH_2CH_2$ | | H | H | $OCH_3$ |

Table 42: When Ar is Ar4, Q is $Q_2$, the substituents of presentitive compounds 42-1 to 42-116 are consistent with 41-1 to 41-116 in Table 41;

Table 43: When Ar is Ar4, Q is $Q_3$, the substituents of presentitive compounds 43-1 to 43-116 are consistent with 41-1 to 41-116 in Table 41;

Table 44: When Ar is Ar4, Q is $Q_4$, the substituents of presentitive compounds 44-1 to 44-116 are consistent with 41-1 to 41-116 in Table 41;

Table 45: When Ar is Ar4, Q is $Q_5$, the substituents of presentitive compounds 45-1 to 45-116 are consistent with 41-1 to 41-116 in Table 41;

Table 46: When Ar is Ar4, Q is $Q_6$, the substituents of presentitive compounds 46-1 to 46-116 are consistent with 41-1 to 41-116 in Table 41;

Table 47: When Ar is Ar4, Q is $Q_7$, the substituents of presentitive compounds 47-1 to 47-116 are consistent with 41-1 to 41-116 in Table 41;

Table 48: When Ar is Ar4, Q is $Q_8$, the substituents of presentitive compounds 48-1 to 48-116 are consistent with 41-1 to 41-116 in Table 41;

Table 49: When Ar is Ar3, Q is $Q_9$, the substituents of presentitive compounds 49-1 to 49-116 are consistent with 41-1 to 41-116 in Table 41;

Table 50: When Ar is Ar3, Q is $Q_{19}$, the substituents of presentitive compounds 50-1 to 50-116 are consistent with 41-1 to 41-116 in Table 41;

Table 51: When Ar is Ar3, Q is $Q_{20}$, the substituents of presentitive compounds 51-1 to 51-116 are consistent with 41-1 to 41-116 in Table 41;

Table 52: When Ar is Ar3, Q is $Q_{21}$, the substituents of presentitive compounds 52-1 to 52-116 are consistent with 41-1 to 41-116 in Table 41;

Table 53: When Ar is Ar3, Q is $Q_{22}$, the substituents of presentitive compounds 53-1 to 53-116 are consistent with 41-1 to 41-116 in Table 41.

Some commercial (or under development) substituent benzyloxy group containing ether compounds used as fungicides in agrochemical field are summarized as follows (Table 54):

| | | | | |
|---|---|---|---|---|
| azoxystrobin | kresoxim-methyl | metominostrobin | picoxystrobin | trifloxstrobin |
| pyraoxystrobin | Dimoxystrobin (SSF 129) | (fluoxastrobin) | orysastrobin | enoxastrobin |
| flufenoxystrobin | (pyrametostrobin) | (triclopyricarb) | fenaminstrobin | pyraclostrobin |

The most preferred substituent benzyloxy group containing ether compounds applied as antitumor drugs of general formula I are: compounds 28-5 (jiaxiangjunzhi), 28-72 (coumoxystrobin), 28-18, 28-128, 28-129 and pyraoxystrobin.

The compounds having formula I in present invention have been reported in prior art, which are commercial available or can be prepared according to the following literatures U.S. Pat. No. 7,642,364, CNP1869032, Pest Manag. Sci. 2011, 67, 647, Nat. Prod. Commun. 2011, 6, 1917, Chin. Chem. Lett. 2011, 22, 663, Chin. J. Pestic. 2011, 50, 90.

The present invention includes the formulations, which were made from the compounds having the general formula I as active ingredient, and preparation thereof. The preparation of formulations: Dissolve the compounds of present invention in water soluble organic solvents, the non-ionicity of surfactant, water soluble lipid, all kinds of cyclodextrin, fatty acid, fatty acid ester, phospholipids or their combination solvents, then 1-20% of carbohydrates were obtained by adding physiological saline. Mentioned organic solvents include polyethylene glycol (PEG), ethanol, propylene glycol or their combination solvents.

The compounds having the general formula I in present invention and their isomers and prodrug can be used to prepare the drugs or formulations to cure, prevent or alleviate cancer. The active ingredients are composed of one or more than two substituent benzyloxy group containing ether compounds having the general formula I. Especially to cure or alleviate the cancer causing by cancer cells of human tissue or organ. The preferred cancers are: colon cancer, liver cancer, lymph cancer, lung cancer, esophageal cancer, breast cancer, central nervous system cancer, melanoma, ovarian cancer, cervical cancer, renal cancer, leukemia, prostatic cancer, pancreatic cancer, bladder cancer, rectal cancer, or stomach cancer, etc.

The compounds in present invention can be used as active ingredients of antitumor drug, which can be used alone or combined with other antitumor/antiviral drugs. The drug combination process in present invention, using at least one of the compounds and its active derivatives with other one or more antitumor/antiviral drugs, are used together to increase the overall effect. The dose and drug administration time of combination therapy are based on the most reasonable treatment effect in the different situations.

The formulations include the effective dose of the compounds having general formula I. The "effective dose" refers to the compound dosage, which are effective to cure cancer. The effective dose or dose can be different based on the suggestions of experienced person at different conditions. For instance, the different usage of drug based on different cancers; the dose of drug also can be changed based on whether it shares with other therapeutic method, such as antitumor or antiviral drugs. The drug can be prepared for any useable formulations. The salts of compounds also can be used if the alkaline or acidic compounds can formed the non-toxic acids or salts. The organic acids/salts in pharmacy include anion salts, which are formed with acids, such as p-toluenesulfonic acid, methylsulfonic acid, acetic acid, benzoic acid, citric acid, malic acid, tartaric acid, maleic acid, succinic acid, ascorbic acid or glycerophosphoric acid; the inorganic salts include chloride, bromide, fluoride, iodide, sulfate, nitrate, bicarbonate, carbonate or phosphate. For example, the alkaline compounds, such as amines can form salts with suitable acids; acids can form salts with alkalis or alkaline earth.

The compounds in present invention having general formula I general easily dissolve in organic solvent, water soluble solvent and their mixture with water. The water soluble solvents prefer alcohol, polyethylene glycol, N-methyl-2-pyrrolidone, N, N-dimethyl acetamide, N, N-dimethyl formamide, dimethylsulfoxide, acetonitrile and their mixture. Mentioned alcohols prefer methanol, ethanol, isopropanol, glycerol or ethylene glycol. The compounds in present invention mix with common drug carrier to form formulations. Dissolve the compounds of present invention in water soluble organic solvents, aprotic solvent, water soluble lipid, cyclodextrin, fatty acid, phospholipids or their combination solvents, then 1-20% of carbohydrates were obtained by adding physiological saline, such as glucose aqueous solution. The stability formulations made by this way are used for animal and clinical.

The drugs were made from the active ingredients of general formula I compounds, which can dose by oral medication or parenteral route, also by implantable medication pump and other methods. Where the parenteral route refer to injection or drip technology through subcutaneous intradermal, intramuscular, intravenous, arteries, atrium, synovium, sternum, intrathecal, wound area, encephalic, etc. The formulations were mixed using conventional method by technicist, which are used for animal and clinical, including tablets, pills, capsule, granule, syrup, injection, freeze-dried powder injection, emulsion, powder, freeze-dried powder, drop pill, milk suspension, aqueous suspension, colloid, colloidal solution, sustained-release suspensions, nanoparticle or other formulations.

The compounds having the general formula I in present invention can be used to cure or alleviate the cancer causing by cancer cells of human tissue or organ. The cancers include but not limited to colon cancer, liver cancer, lymph cancer, lung cancer, esophageal cancer, breast cancer, central nervous system cancer, melanoma, ovarian cancer, cervical cancer, renal cancer, leukemia, prostatic cancer, pancreatic cancer, bladder cancer, rectal cancer or stomach cancer.

DETAILED DESCRIPTION OF THE INVENTION

The present invention is illustrated by the following examples, but without being restricted thereby. (All raw materials are commercially available unless otherwise specified.)

Antitumor Activity Bioassay

In vitro Cell inhibition assay is as follows:

The human cancer cell lines used for this assay were bladder cancer J82, T24, prostate cancer LNCap, PC-3, lung cancer A549, H157, H460, H520, colon cancer HCT8, HCT116, RkO, and leukemia HL-60, etc.

Example 1

In vitro cell culture technology was selected for the determination of inhibition rate bladder cancer cell lines J82 and T24, prostate cancer cell lines LNCap and PC-3, lung cancer cell lines A549, H157, H460 and H520. 1000 to 3000 cells were inoculated to 24-well plate, followed by addition of 1 mL culture medium well known to researchers in this field to each well, the cells were cultured in 5% incubator for 24 hours at 37° C., then the different concentration compounds and controls were added to each well. It should be noted that the added volume is not more than 0.5% of total volume. After completion of addition, the cells continued being cultured in incubator for one week, the culture medium was removed and washed by cold PBS of 1 mL once, and then fixed for 10 minutes at room temperature with 1% formalin, followed by wash with PBS of 1 mL. After fixation, stain was carried out with 0.1% crystal violet for 30 minutes. 0.1% crystal violet was recycled. The stained cells were washed gently with deionized water, dried at room temperature and kepted. The inhibition rate was calculated according to the foiling equation. The controls are Selumetinib (AZD6244), Gefitinib, Cisplatin.

Inhibition rate=number of left cells each treatment/
number of left cells of untreated control×100%

At the concentration of 10 μM, the inhibition rate of compounds of this invention against all tested cell lines attached 90%-100%, some of them were further tested at lower concentration and the comparative bioassay was conducted with the controls selumetinib (AZD6244), gefitinib, Cisplatin at the same time, part of test results are listed in Table 55:

TABLE 55

Inhibition rate on human cancer cells

| Cell line | Compound No | Concentration (μM)/Inhibition (%) | | | | |
|---|---|---|---|---|---|---|
| | | 5.0 | 2.5 | 1.0 | 0.5 | 0.25 |
| J82 | 28-5 | 100 | 100 | 80 | / | / |
| | 28-72 | 100 | 100 | 95 | 90 | 70 |
| | Pyraoxystrobin | 100 | 100 | 100 | 100 | 70 |
| | selumetinib | 70 | / | / | / | / |
| | Cisplatin | 20 | 5 | 0 | 0 | 0 |
| | Compound A | 100 | 100 | 95 | 50 | 0 |
| | Compound B | 100 | 95 | 90 | 50 | 0 |
| | Flufenoxystrobin Azoxystrobin | 0 | / | / | / | / |
| T24 | 28-5 | 100 | 100 | 100 | 100 | 100 |
| | 28-72 | 100 | 100 | 100 | 100 | 100 |
| | Pyraoxystrobin | 100 | 100 | 100 | 100 | 100 |
| | Selumetinib | 70 | / | / | / | / |
| | Cisplatin | 20 | 5 | 0 | 0 | 0 |
| | Compound A | 100 | 100 | 100 | 0 | / |
| | Compourtd B | 100 | 100 | 100 | 5 | 0 |
| | Flufenoxystrobin Azoxystrobin | 0 | / | / | / | / |
| LNCap | 28-5 | 100 | 100 | 100 | / | / |
| | 28-72 | 100 | 100 | 100 | 100 | 100 |
| | Pyraoxystrobin | 100 | 100 | 100 | 100 | 100 |
| | selumetinib | 20 | / | / | / | / |
| | Compound A | 100 | 100 | 100 | 0 | / |
| | Compourtd B | 100 | 50 | 0 | / | / |
| | Flufenoxystrobin Azoxystrobin | 0 | / | / | / | / |
| PC-3 | 28-5 | 100 | 100 | 100 | / | / |
| | 28-72 | 100 | 100 | 100 | 100 | 100 |
| | Pyraoxystrobin | 100 | 100 | 100 | 100 | 100 |
| | Selumetinib | 0 | / | / | / | / |
| | Compound A | 100 | 100 | 85 | 0 | / |
| | Compourtd B | 100 | 100 | 50 | / | / |
| | Flufenoxystrobin Azoxystrobin | 0 | / | / | / | / |
| A549 | 28-5 | 100 | 100 | 80 | / | / |
| | 28-7 | 90 | 70 | / | / | / |
| | 28-12 | 100 | 95 | 80 | / | / |
| | 28-18 | 100 | 100 | 100 | 90 | / |
| | 28-27 | 95 | 90 | 80 | / | / |
| | 28-29 | 95 | / | / | / | / |
| | 28-33 | 99 | 95 | 80 | / | / |
| | 28-34 | 100 | 95 | 90 | / | / |
| | 28-50 | 90 | / | / | / | / |
| | 28-52 | 100 | 100 | 95 | 90 | / |
| | 28-72 | 100 | 100 | 95 | 90 | / |
| | 28-75 | 90 | / | / | / | / |
| | 28-126 | 90 | 85 | / | / | / |
| | 28-128 | 100 | 100 | 100 | 100 | 70 |
| | 28-129 | 100 | 100 | 100 | 95 | 90 |
| | 28-132 | 90 | / | / | / | / |
| | 28-133 | 100 | 100 | / | / | / |
| | 28-134 | 100 | 100 | | | |
| | 28-135 | 80 | / | / | / | / |
| | 28-136 | 100 | 100 | / | / | / |
| | 28-137 | 100 | 100 | / | / | / |
| | 28-137 | 100 | 100 | / | / | / |
| | Selumetinib | 10 | 0 | 0 | 0 | 0 |

TABLE 55-continued

Inhibition rate on human cancer cells

| Cell line | Compound No | Concentration (μM)/Inhibition (%) | | | | |
|---|---|---|---|---|---|---|
| | | 5.0 | 2.5 | 1.0 | 0.5 | 0.25 |
| | Gefitinib | 20 | 10 | 0 | 0 | 0 |
| | Cisplatin | 80 | 30 | 5 | 0 | 0 |
| H157 | 28-5 | 100 | 100 | 100 | 100 | / |
| | 28-72 | 100 | 100 | 100 | 100 | >90 |
| | AZD6244 | 20 | / | / | / | / |
| H460 | 28-2 | 95 | / | / | / | / |
| | 28-5 | 100 | 100 | 100 | 100 | / |
| | 28-7 | 95 | 80 | / | / | / |
| | 28-12 | 95 | 90 | 75 | / | / |
| | 28-18 | 95 | 95 | 95 | 90 | 80 |
| | 28-27 | 95 | 95 | 80 | / | / |
| | 28-29 | 95 | 90 | 70 | / | / |
| | 28-33 | 95 | 95 | 90 | / | / |
| | 28-34 | 95 | 95 | 93 | / | / |
| | 28-41 | 85 | 75 | / | / | / |
| | 28-50 | 95 | 90 | 70 | / | / |
| | 28-52 | 100 | 100 | 100 | 90 | 60 |
| | 28-72 | 100 | 100 | 100 | 100 | 95 |
| | 28-75 | 95 | 90 | 70 | / | / |
| | 28-124 | 75 | / | / | / | / |
| | 28-126 | 95 | 90 | / | / | / |
| | 28-128 | 100 | 100 | 100 | 100 | 80 |
| | 28-129 | 100 | 100 | 95 | 70 | / |
| | 32-5 | 95 | / | / | / | / |
| | 32-6 | 85 | / | / | / | / |
| | Selumetinib | 60 | 0 | 0 | 0 | 0 |
| | Gefitinib | 95 | 0 | 0 | 0 | 0 |
| | Cisplatin | 90 | 30 | 5 | 0 | 0 |
| H520 | 28-5 | 100 | 100 | 90 | 80 | 70 |
| | 28-7 | 100 | 80 | / | / | / |
| | 28-12 | 100 | 100 | 50 | / | / |
| | 28-18 | 100 | 100 | 100 | 95 | 50 |
| | 28-27 | 100 | 100 | 100 | 95 | / |
| | 28-29 | 100 | 70 | 70 | 40 | 30 |
| | 28-33 | 100 | 90 | / | / | / |
| | 28-34 | 100 | 100 | 99 | 70 | / |
| | 28-41 | 70 | / | / | / | / |
| | 28-50 | 100 | 80 | 60 | 50 | 30 |
| | 28-52 | 100 | 100 | 100 | 100 | 70 |
| | 28-72 | 100 | 100 | 100 | 100 | >90 |
| | 28-75 | 100 | 80 | / | / | / |
| | 28-124 | 70 | / | / | / | / |
| | 28-126 | 95 | 90 | 70 | / | / |
| | 28-128 | 100 | 100 | 100 | 100 | 70 |
| | 28-129 | 100 | 100 | 100 | 95 | 85 |
| | Selumetinib | 20 | / | / | / | / |
| | Gefitinib | 5 | 0 | 0 | 0 | 0 |
| | Cisplatin | 50 | 30 | 20 | 5 | 0 |
| HCT 8 | 28-72 | 100 | 100 | 100 | 95 | / |
| | 28-128 | 100 | 100 | 100 | 100 | 95 |
| | 28-129 | 100 | 100 | 100 | 95 | 80 |
| | Selumetinib | 50 | 40 | 20 | / | / |
| | Gefitinib | / | 10 | 5 | 0 | / |
| | Cisplatin | 90 | 70 | 50 | 10 | 5 |
| HCT 116 | 28-72 | 100 | 100 | 99 | 95 | 80 |
| | 28-128 | 100 | 100 | 100 | 100 | 95 |
| | 28-129 | 100 | 100 | 100 | 95 | 90 |
| | Selumetinib | 90 | 85 | 80 | 75 | 50 |
| | Gefitinib | 30 | 5 | 0 | 0 | 0 |
| | Cisplatin | 50 | 20 | 5 | 0 | 0 |
| RkO | 28-72 | 100 | 100 | 100 | 100 | 95 |
| | 28-128 | 100 | 100 | 100 | 100 | 99 |
| | 28-129 | 100 | 100 | 100 | 99 | 85 |
| | Selumetinib | 95 | 90 | 85 | 80 | 30 |
| | Gefitinib | / | 80 | 75 | 70 | 50 |
| | Cisplatin | 70 | 50 | 10 | 5 | 0 |

Note:
1. "/" stands for no data.
2. bladder cancer cell lines J82、T24, prostate cancer cell lines LNCap、PC-3, lung cancer cell lines A549, H157、H460、H520, clon cancer cell lines HCT8, HCT116, RkO, the culture medium for all cell lines is RMPI-1640.

Example 2

The inhibition rate of human leukemia HL-60 cells was evaluated by regular MTT method. The human leukemia HL-60 cells were picked up from cell incubator, after washed for twice using PBS, cells were digested by 0.25% trypsin, and then add medium to terminate the digestion. After cells were collected using centrifuge and re-suspended, counting cells under inverted microscope and adding medium to make a density which was $5\times10^4$ cells/mL. After 100 μL aliquots were added to each well of 96-well microtiter plates, cells were cultured in 5% incubator for overnight at 37° C., then the different concentration compounds were added to each well. After incubation for 48 h, MTT solution was added to each well and plates were then incubated for 4 h. The MTT tetrazolium was reduced to formazan by living cells. Then the formazan crystals were dissolved though adding DMSO to each well. The absorbance was read at 570 nm with a microplate reader.

Part of the test results are listed in Table 56:

TABLE 56

Proliferation inhibitory effect on human leukemia HL-60 cell (%)

| Compound No. | Concentration (μM) | | |
|---|---|---|---|
| | 100 | 10 | 1 |
| 2-1 | 48.8 | 0 | 0 |
| 28-2 | 71.3 | 49.2 | 6.0 |
| 28-3 | 58.8 | 33.4 | 4.1 |
| 28-5 | 73.8 | 59.3 | 31.7 |
| 28-6 | 52.0 | 53.0 | 48.2 |
| 28-7 | 83.9 | 71.0 | 42.3 |
| 28-24 | 86.7 | 44.5 | 10.8 |
| 28-27 | 83.9 | 79.9 | 59.0 |
| 28-38 | 63.7 | 72.9 | 77.5 |
| 28-50 | 84.8 | 83.1 | 47.1 |
| 28-68 | 84.4 | 62.0 | 54.6 |
| 28-71 | 50.3 | 48.2 | 40.9 |
| 28-72 | 54.4 | 47.9 | 45.3 |
| 28-79 | 71.2 | 53.1 | 28.8 |
| 28-124 | 27.8 | 29.3 | 0.5 |
| 28-125 | 85.0 | 73.8 | 47.0 |
| 15-22 | 86.8 | 51.8 | 50.3 |

Note: the culture medium for human leukemia HL-60 is OPTI-MEM.

The invention claimed is:
1. A method of treating a subject having a cancer selected from the group consisting of colon cancer, lung cancer, leukemia, prostatic cancer, and bladder cancer, which comprises administering to the subject a substituent benzyloxy group containing ether compound as an antitumor agent, said substituent benzyloxy group containing either compound having general formula I:

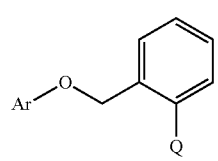

wherein:
Ar is selected from one of the following groups, Ar2 to Ar3:

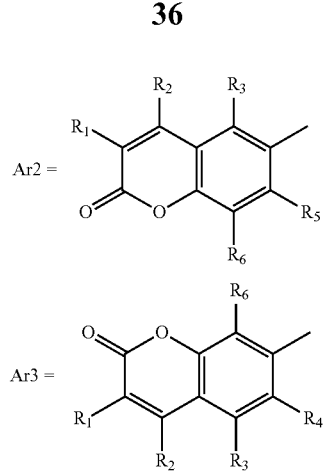

Q is selected from one of the following groups, Q1 to Q22:

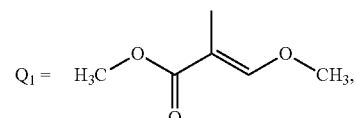
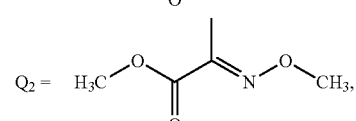
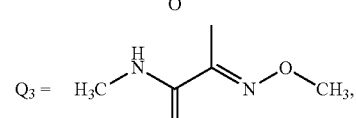
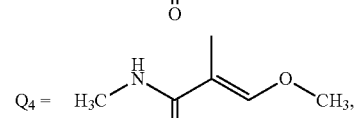
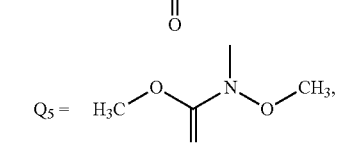
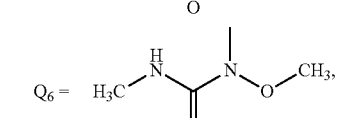
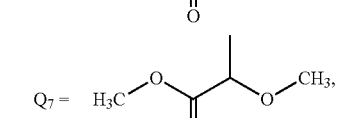
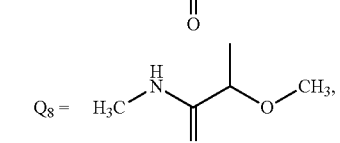
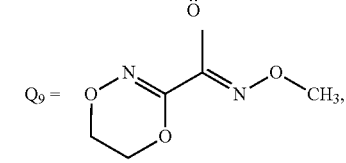

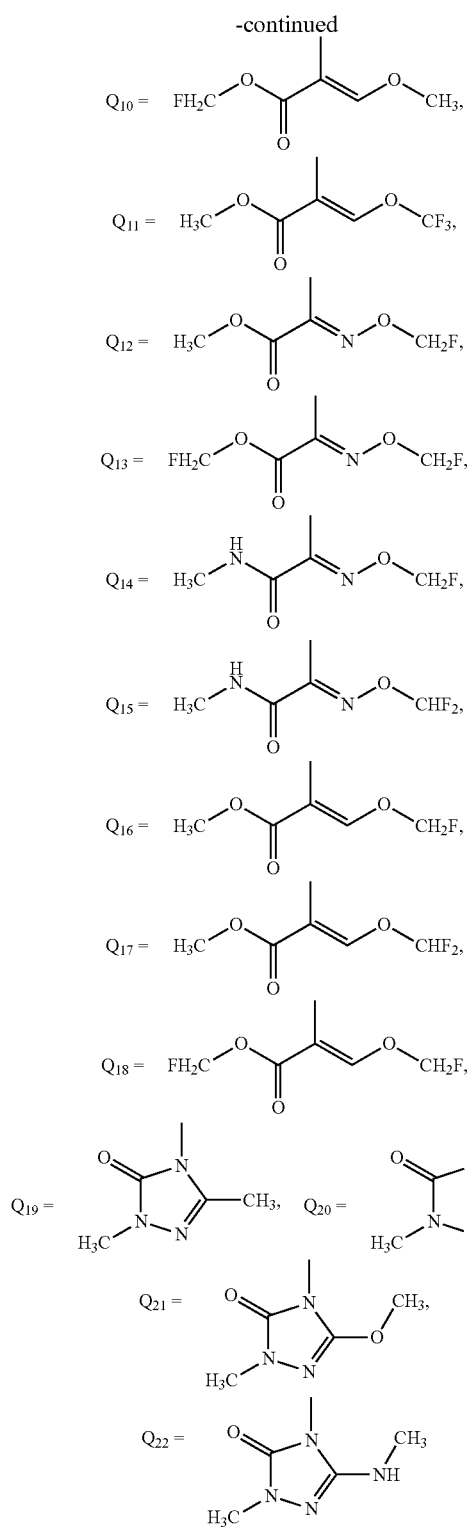

haloC$_1$-C$_{12}$alkylthioC$_1$-C$_{12}$alkyl, C$_1$-C$_{12}$alkylamino, C$_1$-C$_{12}$haloalkylamino, C$_2$-C$_{12}$dialkylamino, C$_2$-C$_{12}$halodialkylamino, piperidinyl, pyrrolidinyl, N-methylpiperidinyl, morpholinyl, C$_2$-C$_{12}$alkenyl, C$_2$-C$_{12}$haloalkenyl, C$_2$-C$_{12}$alkynyl, C$_2$-C$_{12}$haloalkynyl, C$_2$-C$_{12}$alkenyloxy, C$_2$-C$_{12}$haloalkenyloxy, C$_2$-C$_{12}$alkynyloxy, C$_2$-C$_{12}$haloalkynyloxy, C$_1$-C$_{12}$alkylsulfonyl, C$_1$-C$_{12}$haloalkylsulfonyl, C$_1$-C$_{12}$alkylsulfinyl, C$_1$-C$_{12}$haloalkylsulfinyl, C$_1$-C$_{12}$alkylcarbonyl, C$_1$-C$_{12}$haloalkylcarbonyl, C$_1$-C$_{12}$alkylcarbonyloxy, C$_1$-C$_{12}$alkylcarbonylamino, C$_1$-C$_{12}$alkylsulfonyloxy, C$_1$-C$_{12}$alkoxycarbonyl, C$_1$-C$_{12}$haloalkoxycarbonyl, C$_1$-C$_{12}$alkylamlinosulfonyl, C$_1$-C$_{12}$alkoxycarbonylamino, C$_1$-C$_{12}$alkoxycarbonylC$_1$-C$_{12}$alkyl, C$_1$-C$_{12}$alkoxycarbonylC$_1$-C$_{12}$alkoxy, aminoC$_1$-C$_{12}$alkyl, C$_1$-C$_{12}$alkylaminoC$_1$-C$_{12}$alkyl, C$_2$-C$_{12}$dialkylaminoC$_1$-C$_{12}$alkyl, C(=O)NR$_{10}$R$_{11}$, OC(=O)NR$_{10}$R$_{11}$, C(=S)NR$_{10}$R$_{11}$, SO$_2$NR$_{10}$R$_{11}$, C(=NOR$_9$)R$_8$, or R$_7$; or R1 and R2 are linked with a carbon atom to form a six-membered ring;

R$_7$ is unsubstituted or substituted phenyl, phenyloxy, phenyloxy C$_1$-C$_{12}$alkyl, phenylcarbonyl, phenyloxycarbonyl, phenylaminocarbonyl, phenylC$_1$-C$_{12}$alkyl, phenylC$_1$-C$_{12}$alkoxy, phenylC$_1$-C$_{12}$alkoxyC$_1$-C$_{12}$alkyl, naphthyl, naphthyloxy, naphthyloxy C$_1$-C$_{12}$alkyl, naphthylcarbonyl, naphthyl C$_1$-C$_{12}$alkyl, naphthyl C$_1$-C$_{12}$alkoxy, naphthyl C$_1$-C$_{12}$alkoxyC$_1$-C$_{12}$alkyl, heteroaryl, heteroaryloxy, heteroarylC$_1$-C$_{12}$alkoxyC$_1$-C$_{12}$alkyl, heteroaryloxyC$_1$-C$_{12}$alkyl, heteroarylcarbonyl, heteroaryloxycarbonyl, heteroarylaminocarbonyl, heteroarylC$_1$-C$_{12}$alkyl or heteroarylC$_1$-C$_{12}$alkoxy, which may be optionally substituted by 1 to 5 substituents selected from the group consisting of: halo, NO$_2$, CN, SH, C$_1$-C$_6$alkyl, C$_1$-C$_6$haloalkyl, C$_3$-C$_6$cycloalkyl, C$_1$-C$_6$alkoxy, C$_1$-C$_6$haloalkoxy, C$_1$-C$_6$alkylthio, C$_1$-C$_6$haloalkylthio, C$_2$-C$_6$alkenyl, C$_2$-C$_6$haloalkenyl, C$_2$-C$_6$alkynyl, C$_2$-C$_6$haloalkynyl, C$_3$-C$_6$alkenyloxy, C$_3$-C$_6$haloalkenyloxy, C$_3$-C$_6$alkynyloxy, C$_3$-C$_6$haloalkynyloxy, C$_1$-C$_6$alkylsulfinyl, C$_1$-C$_6$haloalkylsulfinyl, C$_1$-C$_6$alkylsulfonyl, C$_1$-C$_6$haloalkylsulfonyl, C$_1$-C$_6$alkoxyC$_1$-C$_6$alkyl, C$_1$-C$_6$alkylcarbonyl, C$_1$-C$_6$haloalkylcarbonyl, C$_1$-C$_6$alkylcarbonyloxy, C$_1$-C$_6$alkylcarbonylamino, C$_1$-C$_6$alkylsulfonyloxy, C$_1$-C$_6$alkoxycarbonyl, C$_1$-C$_6$alkoxyC$_1$-C$_6$alkoxy, C$_1$-C$_6$alkoxycarbonylC$_1$-C$_6$alkyl, C$_1$-C$_6$alkoxycarbonylamino, C$_1$-C$_6$alkoxycarbonylC$_1$-C$_6$alkoxy, CHO, CO$_2$H, CO$_2$Na, CO$_2$NH$_4$, NR$_{10}$R$_{11}$, C(=O)NR$_{10}$R$_{11}$, OC(=O)NR$_{10}$R$_{11}$, C(=S)NR$_{10}$R$_{11}$, and SO$_2$NR$_{10}$R$_{11}$;

R$_8$ and R$_9$ are each independently H, C$_1$-C$_6$alkyl, aryl, or aryl C$_1$-C$_6$alkyl;

R$_{10}$ and R$_{11}$ are each independently H, C$_1$-C$_6$alkyl, C$_1$-C$_6$haloalkyl, C$_1$-C$_6$alkoxy, C$_1$-C$_6$haloalkoxy, C$_1$-C$_6$alkylthio, C$_1$-C$_6$haloalkylthio, or C$_3$-C$_8$cycloalkyl;

and stereoisomers thereof.

2. The method according to claim 1, wherein
Ar is Ar2 or Ar3;
Q is Q$_1$, Q$_2$, Q$_3$, Q$_4$, Q$_5$, Q$_6$, Q$_7$, Q$_8$, Q$_9$, Q$_{11}$, Q$_{20}$, Q$_{21}$, or Q$_{22}$;
R$_1$, R$_2$, R$_3$, R$_4$, R$_5$, and R$_6$ are each independently H, halo, CN, NO$_2$, OH, NH$_2$, CHO, CO$_2$H, CO$_2$Na, CO$_2$NH$_4$, C$_1$-C$_6$alkyl, C$_1$-C$_6$haloalkyl, C$_3$-C$_6$cycloalkyl, C$_1$-C$_6$alkoxy, C$_1$-C$_6$haloalkoxy, C$_1$-C$_6$alkylthio, R$_1$, R$_2$, R$_3$, R$_4$, R$_5$, and R$_6$, are each independently H, halo, CN, NO$_2$, OH, NH$_2$, CHO, CO$_2$H, CO$_2$Na, CO$_2$NH$_4$, C$_1$-C$_{12}$alkyl, C$_1$-C$_{12}$haloalkyl, C$_3$-C$_8$cycloalkyl, C$_1$-C$_{12}$alkoxy, C$_1$-C$_{12}$haloalkoxy, C$_1$-C$_{12}$alkylthio, C$_1$-C$_{12}$haloalkylthio, C$_1$-C$_{12}$alkoxyC$_1$-C$_{12}$alkyl, haloC$_1$-C$_{12}$alkoxyC$_1$-C$_{12}$alkyl, C$_1$-C$_{12}$alkoxyC$_1$-C$_{12}$alkoxy, haloC$_1$-C$_{12}$alkoxyC$_1$-C$_{12}$alkoxy, C$_1$-C$_{12}$alkylthioC$_1$-C$_{12}$alkyl, $C_1$-$C_6$haloalkylthio, $C_1$-$C_6$alkoxy$C_1$-$C_6$alkyl, halo$C_1$-$C_6$alkoxy$C_1$-$C_6$alkyl, $C_1$-$C_6$alkoxy$C_1$-$C_6$alkoxy, halo$C_1$-$C_6$alkoxy$C_1$-$C_6$alkoxy, $C_1$-$C_6$alkylthio$C_1$-$C_6$alkyl, halo$C_1$-$C_6$alkylthio$C_1$-$C_6$alkyl, $C_1$-$C_6$alkylamino, $C_1$-$C_6$haloalkylamino, $C_2$-$C_8$dialkylamino, $C_2$-$C_8$halodialkylamino, piperidinyl, pyrrolidinyl, N-methylpiperidinyl, morpholinyl, $C_2$-$C_6$alkenyl, $C_2$-$C_6$haloalkenyl, $C_2$-$C_6$alkynyl, $C_2$-$C_6$haloalkynyl, $C_2$-$C_6$alkenyloxy, $C_2$-$C_6$haloalkenyloxy, $C_2$-$C_6$alkynyloxy, $C_2$-$C_6$haloalkynyloxy, $C_1$-$C_6$alkylsulfonyl, $C_1$-$C_6$haloalkylsulfonyl, $C_1$-$C_6$alkylsulfinyl, $C_1$-$C_6$haloalkylsulfinyl, $C_1$-$C_6$alkylcarbonyl, $C_1$-$C_6$haloalkylcarbonyl, $C_1$-$C_6$alkylcarbonyloxy, $C_1$-$C_6$alkylcarbonylamino, $C_1$-$C_6$alkylsulfonyloxy, $C_1$-$C_6$alkoxycarbonyl, $C_1$-$C_6$haloalkoxycarbonyl, $C_1$-$C_6$alkylaminosulfonyl, $C_1$-$C_6$alkoxycarbonylamino, $C_1$-$C_6$alkoxycarbonyl$C_1$-$C_6$alkyl, $C_1$-$C_6$alkoxycarbonyl$C_1$-$C_6$alkoxy, amino$C_1$-$C_6$alkyl, $C_1$-$C_6$alkylamino$C_1$-$C_6$alkyl, $C_2$-$C_8$dialkylamino$C_1$-$C_6$alkyl, $C(=O)NR_{10}R_{11}$, $OC(=O)NR_{10}R_{11}$, $C(=S)NR_{10}R_{11}$, $SO_2NR_{10}R_{11}$, $C(=NOR_9)R_8$, or $R_7$; or R1 and R2 are linked with a carbon atom to form a six-membered ring;

$R_7$ is unsubstituted or substituted phenyl, phenyloxy, phenyloxy $C_1$-$C_6$alkyl, phenylcarbonyl, phenyloxycarbonyl, phenylaminocarbonyl, phenyl$C_1$-$C_6$alkyl, phenyl$C_1$-$C_6$alkoxy, phenyl$C_1$-$C_6$alkoxy$C_1$-$C_6$alkyl, naphthyl, naphthyloxy, naphthyloxy $C_1$-$C_6$alkyl, naphthylcarbonyl, naphthyl $C_1$-$C_6$alkyl, naphthyl $C_1$-$C_6$alkoxy, naphthyl$C_1$-$C_6$alkoxy$C_1$-$C_6$alkyl, heteroaryl, heteroaryloxy, heteroaly$C_1$-$C_6$alkoxy$C_1$-$C_6$alkyl, heteroaryloxy$C_1$-$C_6$alkyl, heteroarylcarbonyl, heteroaryloxycarbonyl, heteroarylaminocarbonyl, heteroayl$C_1$-$C_6$alkyl or heteroaryl$C_1$-$C_6$alkoxy, which i may be optionally substituted by 1 to 5 substituents selected from the group consisting of: halo, $NO_2$, CN, SH, $C_1$-$C_4$alkyl, $C_1$-$C_4$ haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$haloalkylthio, $C_2$-$C_4$alkenyl, $C_2$-$C_4$haloalkenyl, $C_2$-$C_4$alkynyl, $C_2$-$C_4$haloalkynyl, $C_3$-$C_4$alkenyloxy, $C_3$-$C_4$haloalkenyloxy, $C_3$-$C_4$alkynyloxy, $C_3$-$C_4$haloalkynyloxy, $C_1$-$C_4$alkylsulfinyl, $C_1$-$C_4$haloalkylsulfinyl, $C_1$-$C_4$alkylsulfonyl, $C_1$-$C_4$haloalkylsulfonyl, $C_1$-$C_4$alkoxy$C_1$-$C_4$alkyl, $C_1$-$C_4$alkylcarbonyl, $C_1$-$C_4$haloalkylcarbonyl, $C_1$-$C_4$alkylcarbonyloxy, $C_1$-$C_4$alkylcarbonylamino, $C_1$-$C_4$alkylsulfonyloxy, $C_1$-$C_4$alkoxycarbonyl, $C_1$-$C_4$alkoxy$C_1$-$C_4$alkoxy, $C_1$-$C_4$alkoxycarbonyl$C_1$-$C_4$alkyl, $C_1$-$C_4$alkoxycarbonylamino, $C_1$-$C_4$alkoxycarbonyl$C_1$-$C_4$alkoxy, CHO, $CO_2H$, $CO_2Na$, $CO_2NH_4$, $NR_{10}R_{11}$, $C(O)NR_{10}R_{11}$, $OC(=O)NR_{10}R_{11}$, $C(=S)NR_{10}R_{11}$, and $SO_2NR_{10}R_{11}$;

$R_8$ and $R_9$ are each independently H, $C_1$-$C_4$alkyl, aryl, or aryl $C_1$-$C_4$alkyl;

$R_{10}$ and $R_{11}$ are each independently H, $C_1$-$C_4$alkyl, $C_1$-$C_4$haloalkyl, $C_1$-$C_4$alkoxy, $C_1$-$C_4$haloalkoxy, $C_1$-$C_4$alkylthio, $C_1$-$C_4$haloalkylthio, or $C_3$-$C_6$cycloalkyl.

3. The method according to claim 2, wherein
Ar is Ar2 or Ar3;
Q is $Q_1$, $Q_2$, $Q_3$, $Q_4$, $Q_5$, $Q_6$, $Q_7$, $Q_8$, $Q_9$, $Q_{19}$, $Q_{20}$, $Q_{21}$, or $Q_{22}$;
$R_1$, $R_2$, $R_3$, $R_4$, $R_5$, and $R_6$ are each independently H, halo, CN, $NO_2$, OH, $NH_2$, CHO, $CO_2H$, $CO_2Na$, $CO_2NH_4$, $C_1$-$C_6$alkyl, $C_1$-$C_6$haloalkyl, $C_3$-$C_6$cycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkoxy$C_1$-$C_4$alkyl, halo$C_1$-$C_4$alkoxy$C_1$-$C_4$alkyl, $C_1$-$C_4$alkoxy$C_1$-$C_4$alkoxy, halo$C_1$-$C_4$alkoxy$C_1$-$C_4$alkoxy, $C_1$-$C_4$alkylthio$C_1$-$C_4$alkyl, halo$C_1$-$C_4$alkylthio$C_1$-$C_4$alkyl, $C_1$-$C_4$alkylamino, $C_1$-$C_4$haloalkylamino, $C_2$-$C_6$dialkylamino, $C_2$-$C_6$halodialkylamino, piperidinyl, pyrrolidinyl, N-methylpiperidinyl, morpholinyl, $C_2$-$C_4$alkenyl, $C_2$-$C_4$haloalkenyl, $C_2$-$C_4$alkynyl, $C_2$-$C_4$haloalkynyl, $C_2$-$C_4$alkenyloxy, $C_2$-$C_4$haloalkenyloxy, $C_2$-$C_4$alkynyloxy, $C_2$-$C_4$haloalkynyloxy, $C_1$-$C_4$alkylsulfonyl, $C_1$-$C_4$haloalkylsulfonyl, $C_1$-$C_4$alkylsulfinyl, $C_1$-$C_4$haloalkylsulfinyl, $C_1$-$C_4$alkylcarbonyl, $C_1$-$C_4$haloalkylcarbonyl, $C_1$-$C_4$alkylcarbonyloxy, $C_1$-$C_4$alkylcarbonylamino, $C_1$-$C_4$alkylsulfonyloxy, $C_1$-$C_4$alkoxycarbonyl, $C_1$-$C_4$haloalkoxycarbonyl, $C_1$-$C_4$alkylaminosulfonyl, $C_1$-$C_4$alkoxycarbonylamino, $C_1$-$C_4$alkoxycarbonyl$C_1$-$C_4$alkyl, $C_1$-$C_4$alkoxycarbonyl$C_1$-$C_4$alkoxy, amino$C_1$-$C_4$alkyl, $C_1$-$C_4$alkylamino$C_1$-$C_4$alkyl, $C_2$-$C_6$dialkylamino$C_1$-$C_4$alkyl, $C(=O)NR_{10}R_{11}$, $OC(=O)NR_{10}R_{11}$, $C(=S)NR_{10}R_{11}$, $SO_2NR_{10}R_{11}$, $C(=NOR_9)R_8$, or $R_7$; or R1 and R2 are linked with a carbon atom to form a saturated six-membered ring;

$R_7$ is unsubstituted or substituted phenyl, phenyloxy, phenyloxy $C_1$-$C_4$alkyl, phenylcarbonyl, phenyloxycarbonyl, phenylaminocarbonyl, phenyl$C_1$-$C_4$alkyl, phenyl$C_1$-$C_4$alkoxy, phenyl$C_1$-$C_4$alkoxy$C_1$-$C_4$alkyl, naphthyl, naphthyloxy, naphthyloxy $C_1$-$C_4$alkyl, naphthylcarbonyl, naphthyl $C_1$-$C_4$alkyl, naphthyl $C_1$-$C_4$alkoxy, naphthyl$C_1$-$C_4$alkoxy$C_1$-$C_4$alkyl, heteroaryl, heteroaryloxy, heteroaryl$C_1$-$C_4$alkoxy$C_1$-$C_4$alkyl, heteroaryloxy$C_1$-$C_4$alkyl, heteroarylcarbonyl, heteroaryloxycarbonyl, heteroarylaminocarbonyl, heteroaryl$C_1$-$C_4$alkyl, or heteroaryl$C_1$-$C_4$alkoxy, which may be optionally substituted by 1 to 5 substituents selected from the group consisting of: halo, $NO_2$, CN, SH, $C_1$-$C_4$alkyl, $C_1$-$C_4$ haloalkyl, $C_3$-$C_6$cycloalkyl, $C_1$-$C_4$alkoxy, $C_1$-$C_4$ haloalkoxy, $C_1$-$C_4$alkylthio, $C_1$-$C_4$haloalkylthio, $C_2$-$C_4$alkenyl, $C_2$-$C_4$haloalkenyl, $C_2$-$C_4$alkynyl, $C_2$-$C_4$haloalkynyl, $C_3$-$C_4$alkenyloxy, $C_3$-$C_4$haloalkenyloxy, $C_3$-$C_4$alkynyloxy, $C_3$-$C_4$haloalkynyloxy, $C_1$-$C_4$alkylsulfinyl, $C_1$-$C_4$haloalkylsulfinyl, $C_1$-$C_4$alkylsulfonyl, $C_1$-$C_4$haloalkylsulfonyl, $C_1$-$C_4$alkoxy$C_1$-$C_4$alkyl, $C_1$-$C_4$alkylcarbonyl, $C_1$-$C_4$haloalkylcarbonyl, $C_1$-$C_4$alkylcarbonyloxy, $C_1$-$C_4$alkylcarbonylamino, $C_1$-$C_4$alkylsulfonyloxy, $C_1$-$C_4$alkoxycarbonyl, $C_1$-$C_4$alkoxy$C_1$-$C_4$alkoxy, $C_1$-$C_4$alkoxycarbonyl$C_1$-$C_4$alkyl, $C_1$-$C_4$alkoxycarbonylamino, $C_1$-$C_4$alkoxycarbonyl$C_1$-$C_4$alkoxy, CHO, $CO_2H$, $CO_2Na$, $CO_2NH_4$, $NR_{10}R_{11}$, $C(=O)NR_{10}R_{11}$, $OC(=O)NR_{10}R_{11}$, $C(=S)NR_{10}R_{11}$, and $SO_2NR_{10}R_{11}$;

$R_8$ and $R_9$ is are each independently H, $C_1$-$C_4$alkyl, aryl, or aryl $C_1$-$C_4$alkyl;

$R_{10}$ and $R_{11}$ are each independently H, $C_1$-$C_4$alkyl, $C_1$-$C_4$ haloalkyl, $C_1$-$C_4$alkoxy, $C_1$-$C_4$ haloalkoxy, $C_1$-$C_4$alkylthio, $C_1$-$C_4$ haloalkylthio, or $C_3$-$C_6$cycloalkyl.

4. The method according to claim 3, wherein
Ar is Ar2 or Ar3;
Q is $Q_1$, $Q_2$, $Q_3$, $Q_4$, $Q_5$, $Q_6$, $Q_7$, or $Q_8$;
$R_1$, $R_2$, $R_3$, $R_4$, $R_5$, and $R_6$ are each independently H, halo, CN, $C_1$-$C_6$alkyl, $C_1$-$C_4$haloalkyl, $C_3$-$C_6$cycloalkyl, $C_1$-$C_4$alkoxy, $C_1$-$C_4$haloalkoxy, $C_1$-$C_4$alkylthio, A $C_1$-$C_4$alkoxy$C_1$-$C_4$alkyl, $C_1$-$C_4$alkylamino, $C_2$-$C_6$dialkylamino, $C_1$-$C_4$alkylsulfonyl, or $R_7$; or R1 and R2 are linked with a carbon atom to form a saturated six-membered ring;

$R_7$ is unsubstituted or substituted phenyl, benzyl, phenylethyl or heteroaryl, which may be optionally substituted by 1 to 5 substituents selected from the group consisting of: halo, $NO_2$, CN, $C_1$-$C_4$alkyl, $C_1$-$C_4$ haloalkyl, $C_1$-$C_4$alkoxy, and $C_1$-$C_4$ haloalkoxy.

5. The method according to claim 4, wherein
Ar is Ar2 or Ar3;
Q is $Q_1$;
$R_1$, $R_2$, $R_3$, $R_4$, $R_5$, and $R_6$ are each independently H, halo, CN, $C_1$-$C_6$alkyl, $C_1$-$C_4$haloalkyl, or $R_7$; or R1 and R2 are linked with a carbon atom to form a saturated six-membered ring;
$R_7$ is unsubstituted or substituted phenyl, benzyl, or heteroaryl, which may be optionally substituted by 1 to 5 substituents selected from the group consisting of: halo, $NO_2$, CN, $C_1$-$C_4$alkyl, $C_1$-$C_4$ haloalkyl, $C_1$-$C_4$alkoxy, and $C_1$-$C_4$ haloalkoxy.

6. The method according to claim 5, wherein
Ar is Ar3;
Q is $Q_1$;
$R_1$, $R_2$, $R_3$, $R_4$, $R_5$, and $R_6$ are each independently H, halo, CN, $C_1$-$C_6$alkyl, $C_1$-$C_4$haloalkyl, or $R_7$; or R1 and R2 are linked with a carbon atom to form a saturated six-membered ring;
$R_7$ is unsubstituted or substituted phenyl, benzyl, or heteroaryl, which may be optionally substituted by 1 to 5 substituents selected from the group consisting of: halo, $NO_2$, CN, $C_1$-$C_4$alkyl, $C_1$-$C_4$ haloalkyl, $C_1$-$C_4$alkoxy, and $C_1$-$C_4$ haloalkoxy.

7. The method according to claim 6, wherein
Ar is Ar3;
Q is $Q_1$;
$R_1$ is H, halo, or $C_1$-$C_6$alkyl;
$R_2$ is $C_1$-$C_4$alkyl, $C_1$-$C_4$haloalkyl, or $R_7$;
or R1 and R2 are linked with a carbon atom to form a saturated six-membered ring;
$R_3$ and $R_4$ are H;
$R_6$ is H or $C_1$-$C_4$alkyl;
$R_7$ is unsubstituted or substituted phenyl, which may be optionally substituted by 1 to 3 substituents selected from the group consisting of: halo, CN, $C_1$-$C_4$alkyl, $C_1$-$C_4$ haloalkyl, $C_1$-$C_4$alkoxy, and $C_1$-$C_4$ haloalkoxy.

8. The method according to claim 7, wherein
Ar is Ar3;
Q is $Q_1$;
$R_1$ is H, halo, or $C_1$-$C_6$alkyl;
$R_2$ is $C_1$-$C_4$alkyl or $R_7$;
or R1 and R2 are linked with a carbon atom to form a saturated six-membered ring;
$R_3$ and $R_4$ are H;
$R_6$ is H or $C_1$-$C_4$alkyl;
$R_7$ is unsubstituted or substituted phenyl, which may be optionally substituted by 1 to 2 substituents selected from the group consisting of: halo, $C_1$-$C_4$alkyl, $C_1$-$C_4$alkoxy, and $C_1$-$C_4$ haloalkoxy.

9. The method according to claim 8, wherein
Ar is Ar3;
Q is $Q_1$;
$R_1$ is H, F, or $C_1$-$C_4$alkyl;
$R_2$ is $C_1$-$C_4$alkyl or phenyl;
or $R_1$ and $R_2$ are linked with a carbon atom to form a saturated six-membered ring;
$R_3$ and $R_4$ are H;
$R_6$ is H or $CH_3$.

10. The method according to claim 9, wherein
Ar is Ar3;
Q is $Q_1$;
$R_1$ is H or $C_1$-$C_4$alkyl;
$R_2$ is $CH_3$ or phenyl;
or $R_1$ and $R_2$ are linked with a carbon atom to form a saturated six-membered ring;
$R_3$, $R_4$, $R_6$ are H.

11. The method according to claim 1, wherein the substituent benzyloxy group containing ether compound is administered, as an active ingredient, orally or parentally, or by implantable medication pump administration.

12. The method according to claim 11, wherein the substituent benzyloxy group containing ether compound is administered as an active ingredient in the form of a tablet, a pill, a capsule, a granule, a syrup, an injection, or a freeze-dried powder injection.

13. The method according to claim 12, two or more of the substituted benzyloxy group containing ether compounds are provided as me active ingredient.

\* \* \* \* \*